US010125357B2

(12) United States Patent
Seifried et al.

(10) Patent No.: US 10,125,357 B2
(45) Date of Patent: Nov. 13, 2018

(54) FACTOR IX VARIANTS WITH CLOTTING ACTIVITY IN ABSENCE OF THEIR COFACTOR AND THEIR USE FOR TREATING BLEEDING DISORDERS

(75) Inventors: Erhard Seifried, Königstein (DE); Jörg Schüttrumpf, Frankfurt am Main (DE)

(73) Assignee: DRK-BLUTSPENDEDIENST BADEN-WÜRTTEMBERG-HESSEN GGMBH, Frankfurt am Main (DE)

( * ) Notice: Subject to any disclaimer, the term of this patent is extended or adjusted under 35 U.S.C. 154(b) by 1145 days.

(21) Appl. No.: 13/001,187

(22) PCT Filed: Jul. 28, 2009

(86) PCT No.: PCT/EP2009/005465
§ 371 (c)(1),
(2), (4) Date: May 19, 2011

(87) PCT Pub. No.: WO2010/012451
PCT Pub. Date: Feb. 4, 2010

(65) Prior Publication Data
US 2011/0217284 A1 Sep. 8, 2011

(30) Foreign Application Priority Data
Jul. 28, 2008 (EP) .................................... 08013561

(51) Int. Cl.
*C12N 9/64* (2006.01)
(52) U.S. Cl.
CPC ...... *C12N 9/644* (2013.01); *C12Y 304/21022* (2013.01)
(58) Field of Classification Search
None
See application file for complete search history.

(56) References Cited

U.S. PATENT DOCUMENTS

| 2006/0040856 A1* | 2/2006 | DeFrees et al. ................. 514/8 |
| 2008/0167219 A1 | 7/2008 | Lin et al. |
| 2008/0214461 A1* | 9/2008 | Dockal et al. ................. 514/12 |
| 2008/0214462 A1* | 9/2008 | Dockal et al. ................. 514/12 |

FOREIGN PATENT DOCUMENTS

| WO | WO 99/03496 | 1/1999 |
| WO | WO 2007/149406 | 12/2007 |
| WO | WO 2008/092643 | 8/2008 |
| WO | WO 2008/092644 | 8/2008 |
| WO | WO 2008/118507 | 10/2008 |
| WO | WO 2010012251 A1 * | 2/2010 |

OTHER PUBLICATIONS

Hopfner K-P., et al. 1997 The EMBO Journal 16(22): 6626-6635.*
Chang, J. et al., "Changing residue 338 in human factor IX from arginine to alanine causes an increase in catalytic activity", *Journal of Biological Chemistry*, May 1998, vol. 273, No. 20, pp. 12089-12094.
Chang, Y. et al., "Identification of functionally important residues of the epidermal growth factor-2 domain of factor IX by alanine-scanning mutagenesis", *Journal of Biological Chemistry*, Jul. 2002, vol. 277, No. 28, pp. 25393-25399.
Hamaguchi et al., "Mutations in the catalytic domain of factor IX that are related to the subclass hemophilia Bm", *Biochemistry*, Jun. 1993, vol. 32, No. 25, pp. 6324-6329.
Hartmann et al., "Variants of recombinant factor IX with enhanced functional properties", *Blood*, Nov. 2007, vol. 110, No. 11, part 1, abstract 2694.
Kolkman et al., "Insertion loop 256-268 in coagulation factor IX restricts enzymatic activity in the absence but not in the presence of factor VIII", *Biochemistry*, Jun. 2000, vol. 39, No. 25, pp. 7398-7405.
Lin et al., "Identification of functionally important residues in the protease domain of factor IX that are critical for binding factor XIa, TFPI, and antibodies", *Blood*, Nov. 2002, vol. 100, No. 11, abstract 1006.
Sichler et al., "Physiological fIXa activation involves a cooperative conformational rearrangement of the 99-loop", *Journal of Biological Chemistry*, Feb. 2003, vol. 278, No. 6, pp. 4121-4126.
Yoshioka et al., "Congenital factor IX abnormalities", Database Capulus, Chemical Abstracts Service, Database Accession No. 1991:245177, 1990, XP-002516994.

* cited by examiner

*Primary Examiner* — Marsha Tsay
(74) *Attorney, Agent, or Firm* — Saliwanchik, Lloyd & Eisenschenk

(57) ABSTRACT

The present invention relates to variants of a vitamin K-dependent serine protease of the coagulation cascade, preferably variants of factor IX (F.IX), wherein the variant is characterized in that it has clotting activity in absence of its cofactor. The present invention furthermore relates to the use of these variants for the treatment and/or prophylaxis of bleeding disorders, in particular hemophilia A and/or hemophilia B or hemophilia caused or complicated by inhibitory antibodies to F.VIII. The present invention also relates to further variants of factor IX (F.IX) which have desired properties and can, thus be tailored for respective specific therapeutic applications.

18 Claims, 8 Drawing Sheets
Specification includes a Sequence Listing.

Figure 1

```
1     Met Gln Arg Val Asn Met Ile Met Ala Glu Ser Pro Gly Leu Ile Thr Ile Cys Leu Leu Gly Tyr Leu Leu
1     ATG CAG CGC GTG AAC ATG ATC ATG GCA GAA TCA CCA GGC CTC ATC ACC ATC TGC CTT TTA GGA TAT CTA CTC

Y1A
25    Ser Ala Glu Cys Thr Val Phe Leu Asp His Glu Asn Ala Asn Lys Ile Leu Asn Arg Pro Lys Arg Ala Asn
73    AGT GCT GAA TGT ACA GTT TTT CTT GAT CAT GAA AAC GCC AAC AAA ATT CTG AAT CGG CCA AAG AGG GCT AAT

G4Y                  V10K                                                            P25Y
49    Ser Tyr Lys Leu Glu Glu Phe Lys Gln Gly Asn Leu Glu Arg Glu Cys Met Glu Glu Lys Cys Ser Tyr Glu
145   TCA TAT AAA TTG GAA GAG TTT AAG CAA GGG AAC CTT GAG AGA GAA TGT ATG GAA GAA AAG TGT AGT TAT GAA

N34D T35D  R37T                                             Q50P
73    Glu Ala Arg Glu Val Phe Glu Asp Asp Glu Thr Thr Thr Glu Phe Trp Lys Gln Tyr Val Asp Gly Asp Pro
218   GAA GCA CGA GAA GTT TTT GAA GAC GAT GAA ACG ACA ACT GAA TTT TGG AAG CAG TAT GTT GAT GGA GAT CCG

97    Cys Glu Ser Asn Pro Cys Leu Asn Gly Gly Ser Cys Lys Asp Asp Ile Asn Ser Tyr Glu Cys Trp Cys Pro
291   TGT GAG TCC AAT CCA TGT TTA AAT GGC GGC AGT TGC AAG GAT GAC ATT AAT TCC TAT GAA TGT TGG TGT CCC

D85A V86A
121   Phe Gly Phe Glu Gly Lys Asn Cys Glu Leu Ala Val Thr Cys Asn Ile Lys Asn Gly Arg Cys Glu Gln Phe
364   TTT GGA TTT GAA GGA AAG AAC TGT GAA TTA GCT GCA ACA TGT AAC ATT AAG AAT GGC AGA TGC GAG CAG TTT

R116A         E119A N120A
145   Cys Lys Asn Ser Ala Asp Asn Lys Val Val Cys Ser Cys Thr Glu Gly Tyr Ala Leu Ala Ala Ala Gln Lys
437   TGT AAA AAT AGT GCT GAT AAC AAG GTG GTT TGC TCC TGT ACT GAG GGA TAT GCA CTT GCA GCA GCC CAG AAG

169   Ser Cys Glu Pro Ala Val Pro Phe Pro Cys Gly Arg Val Ser Val Ser Gln Thr Ser Lys Leu Thr Arg Ala
510   TCC TGT GAA CCA GCA GTG CCA TTT CCA TGT GGA AGA GTT TCT GTT TCA CAA ACT TCT AAG CTC ACC CGT GCT

193   Glu Thr Val Phe Pro Asp Val Asp Tyr Val Asn Ser Thr Glu Ala Glu Thr Ile Leu Asp Asn Ile Thr Gln
583   GAG ACT GTT TTT CCT GAT GTG GAC TAT GTA AAT TCT ACT GAA GCT GAA ACC ATT TTG GAT AAC ATC ACT CAA

V181I
217   Ser Thr Gln Ser Phe Asn Asp Phe Thr Arg Ile Val Gly Gly Glu Asp Ala Lys Pro Gly Gln Phe Pro Trp
656   AGC ACC CAA TCA TTT AAT GAC TTC ACG CGT ATT GTT GGT GGA GAA GAT GCC AAA CCA GGT CAA TTC CCT TGG

V217L
241   Gln Val Val Leu Asn Gly Lys Val Asp Ala Phe Cys Gly Gly Ser Ile Val Asn Glu Lys Trp Ile Leu Thr
729   CAG GTT GTT TTG AAT GGT AAA GTT GAT GCA TTC TGT GGA GGC TCT ATC GTT AAT GAA AAA TGG ATT TTA ACT

E235K
265   Ala Ala His Cys Val Glu Thr Gly Val Lys Ile Thr Val Val Ala Gly Lys His Asn Ile Glu Glu Thr Glu
802   GCT GCC CAC TGT GTT GAA ACT GGT GTT AAA ATT ACA GTT GTC GCC GGC AAA CAT AAT ATT GAG GAG ACA GAA

E245V                      I253V                Y259F                    K265T
289   His Thr Val Gln Lys Arg Asn Val Ile Arg Val Ile Pro His His Asn Phe Asn Ala Ala Ile Asn Thr Tyr
875   CAT ACA GTG CAA AAG CGA AAT GTG ATT CGA GTT ATT CCT CAC CAC AAC TTC AAT GCA GCT ATT AAT ACG TAC

E274K         E277A                                                      I290P
313   Asn His Asp Ile Ala Leu Leu Lys Leu Asp Glu Pro Leu Val Leu Asn Ser Tyr Val Thr Pro Ile Cys Leu
948   AAC CAT GAC ATT GCC CTT CTG AAA CTG GAC GCA CCC TTA GTG CTA AAC AGC TAC GTT ACA CCT ATT TGC CTT

A291P                      K301I  G303E
337   Pro Asp Lys Glu Tyr Thr Asn Ile Phe Leu Ile Phe Glu Ser Gly Tyr Val Ser Gly Trp Gly Arg Val Phe
1021  CCT GAC AAG GAA TAC ACG AAC ATC TTC CTC ATA TTT GAA TCT GGC TAT GTA AGT GGC TGG GGA AGA GTC TTC

R338A
361   His Lys Gly Arg Ser Ala Leu Val Leu Gln Tyr Leu Arg Val Pro Leu Val Asp Arg Ala Thr Cys Leu Ala
1094  CAC AAA GGG AGA TCA GCT TTA GTT CTT CAG TAC CTT AGA GTT CCA CTT GTT GAC CGA GCC ACA TGT CTT GCA

T340S                  Y345T                            F353Y             R358A     S360A
385   Ser Ser Lys Phe Thr Ile Thr Asn Asn Met Phe Cys Ala Gly Tyr His Glu Gly Gly Ala Asp Ala Cys Gln
1167  TCT TCA AAG TTC ACC ATC ACT AAC AAC ATG TTC TGT GCT GGC TAT CAT GAA GGA GGT GCA GAT GCA TGT CAA

G375F  S377W                  I383V
409   Gly Asp Ser Gly Gly Pro His Val Thr Glu Val Glu Phe Thr Trp Phe Leu Thr Gly Ile Val Ser Trp Gly
1240  GGA GAT AGT GGG GGA CCC CAT GTT ACT GAA GTG GAA TTC ACC TGG TTC TTA ACT GGA ATT GTT AGC TGG GGT

E388G
433   Glu Gly Cys Ala Met Lys Gly Lys Tyr Gly Ile Tyr Thr Lys Val Ser Arg Tyr Val Asn Trp Ile Lys Glu
1313  GAA GGG TGT GCA ATG AAA GGC AAA TAT GGA ATA TAT ACC AAG GTA TCC CGG TAT GTC AAC TGG ATT AAG GAA

457   Lys Thr Lys Leu Thr ***
1386  AAA ACA AAG CTC ACT TAA
```

Figure 8

FACTOR IX VARIANTS WITH CLOTTING ACTIVITY IN ABSENCE OF THEIR COFACTOR AND THEIR USE FOR TREATING BLEEDING DISORDERS

CROSS REFERENCE TO A RELATED APPLICATION

This application is a National Stage Application of International Application Number PCT/EP2009/005465, filed Jul. 28, 2009; which claims priority to European Application No. 08013561.9, filed Jul. 28, 2008; which are incorporated herein by reference in their entirety.

The present invention relates to variants of a vitamin K-dependent serine protease of the coagulation cascade, preferably variants of factor IX (F.IX), wherein the variant is characterized in that it has clotting activity in absence of its cofactor. The present invention furthermore relates to the use of these variants for the treatment and/or prophylaxis of bleeding disorders, in particular hemophilia A and/or hemophilia B or hemophilia caused or complicated by inhibitory antibodies to F.VIII. The present invention also relates to further variants of factor IX (F.IX) which have desired properties and can, thus be tailored for respective specific therapeutic applications.

BACKGROUND OF THE INVENTION

Coagulation Factor IX

The blood coagulation factor IX (F.IX) plays a central role in the coagulation cascade. F.IX is a trypsin-like vitamin K-dependent serine protease that circulates in the plasma as a single chain inactive zymogen (DiScipio et al., 1977; Davie et al., 1991). Factor IX is activated by either factor XIa or by factor VIIa-tissue factor in a $Ca^{2+}$ dependent manner. The activation requires cleavage of two peptide bonds by either the activated factor VII (F.VIIa)-tissue factor complex or activated factor XI (F.XIa) (Fujikawa et al., 1974; Lindquist et al., 1978) to remove a 35-residue activation peptide.

F.IX is a multi-domain protein. An N-terminal γ-carboxy glutamic acid (GLA) domain is followed by two epidermal growth factor-like (EGF) repeats, the activation peptide (AP) and a C-terminal serine protease domain with a trypsin-like active site (DiScipio et al., 1978). This domain structure defines the serine protease family of clotting factors (Furie and Furie, 1988), including also factor II (F.II), factor VII (F.VII), factor X (F.X), factor XI (F.XI), factor XII (F.XII), and protein C (PC). Within this family, F.IXa has unique proteolytic properties. Complex formation of F.IXa with F.VIIIa on a phospholipid surface increases reactivity against the natural substrate F.X $10^6$-fold (Duffy and Lollar, 1992), while virtually no cleavage of peptides with corresponding F.X sequences was observed (McRae et al., 1981). Activated factor IX (F.IXa) then activates factor X (F.X) in a reaction that is dependent on the presence of calcium ions, a membrane surface (phospholipid), and a nonenzymatic protein cofactor, activated factor VIII (F.VIIIa) (Davie et al., 1991).

The importance of F.IXa in hemostasis is reflected by the occurrence of the bleeding disorder hemophilia B in individuals carrying mutations in the F.IX gene (Gianelli et al., 1998). F.IXa displays only very little proteolytic activity against natural or synthetic substrates in the absence of its cofactor F.VIIIa. Binding of F.VIIIa results in a $10^6$-fold increase in proteolytic activity for F.X, whereas the activity with peptidic substrates remains less affected (Duffy and Lollar, 1992; McRae et al., 1981). The latter substrate-dependent activity of F.IXa modulation is similarly observed for the related coagulation enzymes activated PC (co-factor Protein S), F.Xa (co-factor Factor Va), F.VIIa (cofactor tissue factor), and FIIa (co-factor thrombomodulin), which in the presence of their cofactors, achieve a significant activity or specificity change with their natural substrates. (Mann et al. 2003). All coagulation serine proteases share extensive structural and functional homology.

Furthermore, the coagulation factors IXa (F.IXa) and Xa (F.Xa) both cleave natural substrates effectively only with a cofactor at a phospholipid surface. Hopfner et al. (1997) investigated variants of truncated F.IXa (rf9a) and F.Xa (rf10a) in *E. coli* to identify determinants of the difference in the amidolytic activity of F.IXa which is $10^4$-fold lower than that of F.Xa. Based on the crystal structures of F.IXa and F.Xa four characteristic active site components (namely Glu219, the 148-loop, Ile213, the 99-loop, based on chymotrypsin numbering) were subsequently exchanged between rf9a and rf10a. Furthermore, combining all four mutations essentially introduced F.Xa properties into rf9a, i.e. the amidolytic activity was increased 130-fold with F.Xa substrate selectivity.

Enzymatically, F.IXa is characterized by its very low amidolytic activity that is not improved in the presence of cofactor, factor VIIIa (F.VIIIa), distinguishing F.IXa from all other coagulation factors. Activation of the F.IXa-F.VIIIa complex requires its macromolecular substrate, factor X (F.X). The 99-loop positioned near the active site partly accounts for the poor activity of F.IXa because it adopts a conformation that interferes with canonical substrate binding in the subsites S2-S4. Sichler et al. (2003) disclose that residues Lys-98 and Tyr-99 (chymotrypsin numbering) are critically linked to the amidolytic properties of F.IXa. Exchange of Tyr-99 with smaller residues resulted not only in an overall decreased activity but also in impaired binding in S1. Replacement of Lys-98 with smaller and uncharged residues increased activity. Simultaneous mutagenesis of Lys-98, Tyr-177, and Tyr-94 (rf9-Y94F/K98T/Y177T, chymotrypsin numbering)) produced an enzyme with 7000-fold increased activity and altered specificity towards factor Xa. Sichler et al. (2003) concluded, that these residues account for the low factor IXa activity. Sichler et al. (2003) concluded, that this triple mutant rf9-Y94F/K98T/Y177T (chymotrypsin numbering) probably mimics the conformational changes that are physiologically induced by cofactor and substrate binding.

Hemophilia

The best-known coagulation factor disorders are the hemophilias. Hemophilia is the name of a family of hereditary genetic disorders that impair the body's ability to control blood clotting, or coagulation. Haemophilia A, the most common form, is caused by a mutation of the factor VIII (F.VIII) gene, leading to a deficiency in F.VIII. The inheritance is X-linked recessive; hence, males are affected while females are carriers or very rarely display a mild phenotype. 1 in 5,000 males are affected. Hemophilia B, also known as factor IX (F.IX) deficiency, is the second most common type of hemophilia, but hemophilia B is far less common than hemophilia A.

These genetic deficiencies may lower blood plasma clotting factor levels of coagulation factors needed for a normal clotting process. When a blood vessel is injured, a temporary scab does form, but the missing coagulation factors prevent fibrin formation which is necessary to maintain the blood clot. Thus a haemophiliac does not bleed more intensely than a normal person, but for a much longer amount of time.

In severe haemophiliacs even a minor injury could result in blood loss lasting days, weeks, or not ever healing completely. The critical risk here is with normally small bleeds which due to missing F.VIII take long times to heal. In areas such as the brain or inside joints this can be fatal or life debilitating. The bleeding with external injury is normal, but incidence of late re-bleeding and internal bleeding is increased, especially into muscles, joints, or bleeding into closed spaces. Major complications include hemarthrosis, hemorrhage, gastrointestinal bleeding, and menorrhagia.

Though there is no cure for haemophilia, it can be controlled with regular infusions of the deficient clotting factor, i.e. F.VIII in haemophilia A or F.IX in haemophilia B.

In western countries, common standards of care for hemophilia fall into one of two categories: (i) prophylaxis or (ii) on-demand. Prophylaxis involves the infusion of coagulation factor on a regular schedule in order to keep clotting levels sufficiently high to prevent spontaneous bleeding episodes. On-demand treatment involves treating bleeding episodes once they arise.

However, some haemophiliacs develop antibodies (inhibitors) against the replacement factors given to them, so the amount of the factor has to be increased or non-human replacement products must be given, such as porcine F.VIII or modified variants thereof, see e.g. WO 01/68109 A1 (Emory University).

If a patient becomes refractory to replacement coagulation factor as a result of circulating inhibitors, this may be overcome with recombinant human factor VII (Novo-Seven®), see also EP 1 282 438 B1 and EP 1 282 439 B1 (Novo Nordisk). A limitation of this approach so far is the short half life of factor VIIa (2 to 3 hours) compared to factor VIII (10 to 14 hours) or factor IX (18 to 30 hours), respectively and depending on the preparation, which makes prophylactic therapy with factor VIIa difficult. Further, the risks of using an already activated protease, like factor VIIa, over prolonged time intervals might carry risks, including thrombotic risks, risks through constant activation of the vascular endothelium and vessel damage, risk of pro-coagulant signalling which could promote tumor growth or metastasis, etc.

WO 02/40544 A2 discloses mutant human factor IX comprising mutations in the heparin binding domain, which decrease the affinity of the mutant human F.IX for heparin compared to wild type F.IX, and their use in the therapeutic intervention of hemophilia B.

Gene Therapy

Hemophilia is ideal for a gene therapeutic approach since the required coagulation is circulating in the blood stream and may therefore be expressed basically everywhere in the body. Further, studies with prophylactic treatment of patients with a severe form of the disease have demonstrated that a minimal elevation of circulating coagulation factor above 1% can already improve the clinical outcome and avoid the majority of lesions caused by the disease, i.e. joint destruction. Several gene therapy approaches have been developed, but testing is still in the early clinical stages. The most promising approaches are currently for the treatment of hemophilia B with adeno-associated viral vectors (AAV).

Intramuscular injection AAV to skeletal muscle of humans with hemophilia B is safe, but higher doses are required to achieve therapeutic factor IX levels. However, dose escalation is not possible in this approach, since the risk of the formation of inhibitory antibodies depends on the amount of F.IX antigen expressed in the muscle per injection site. Estimation in a hemophilia B dog model let to the conclusion, that more then 400 intramuscular injections would be necessary to obtain F.IX expression levels of around 1% in humans (Arruda et al., 2004). This procedure, therefore, is not applicable to humans. The efficacy of this approach is hampered by the retention of F.IX in muscle extracellular spaces and by the limiting capacity of muscle to synthesize fully active F.IX at high expression rates. To overcome these limitations, Schuettrumpf et al. (2005) constructed AAV vectors encoding F.IX variants for muscle- or liver-directed expression in hemophilia B mice. Circulating F.IX levels following intramuscular injection of AAV-F.IX-K5A/V10K (F.IX numbering), a variant with low-affinity to extracellular matrix, were 2-5 fold higher compared with wild-type (WT) F.IX, while the protein-specific activities remained similar. Expression of F.IX-R338A generated a protein with 2- or 6-fold higher specific activity than F.IX-WT following vector delivery to skeletal muscle or liver, respectively. F.IX-WT and variant forms provide effective hemostasis in vivo upon challenge by tail-clipping assay. Importantly, intramuscular injection of AAV-F.IX variants did not trigger antibody formation to F.IX in mice tolerant to F.IX-WT. Besides of the mentioned R338A variant, first described by Chang et al. (1998), another variant, V86A, with higher specific F.IX activity has been described (Chang et al. 2002).

The application of gene therapy strategies for hemophilia A in comparison to hemophilia B is further complicated by the higher immunogenicity and the bigger size of the F.VIII compared to F.IX.

Thus, there is a need in the art for providing improved means and methods for the treatment and/or prophylaxis of bleeding disorders, in particular hemophilia A and/or B.

Thus, the present invention aims to improve the methods and means for the treatment and/or prophylaxis of bleeding disorders as present in the prior art and it is, thus, an objective of the present invention to provide improved methods and means which allow for an effective, specific and targeted treatment and/or prophylaxis of bleeding disorders, in particular hemophilia A and/or B.

According to the present invention this object is solved by providing a variant of a vitamin K-dependent serine protease of the coagulation cascade wherein the variant is characterized in that it has clotting activity in absence of its cofactor.

The coagulation factors VII (F.VII), IX (F.IX) and X (F.X) as well as the cofactor inhibitor protein C (which degrades the co-factors F.Va and F.VIIIa) and thrombin are vitamin K-dependent serine proteases of the coagulation cascade. Vitamin K is an essential factor to a hepatic gamma-glutamyl carboxylase that adds a carboxyl group to glutamic acid residues (in the Gla-domain) on factors II (thrombin), VII, IX and X, as well as protein S, protein C and protein Z.

As discussed above, the serine protease family of clotting factors, which includes factor II (F.II), factor VII (F.VIII), factor IX (F.IX), factor X (F.X), and protein C (PC), is defined by a specific domain structure (Furie and Furie, 1988).

Serine proteases are characterised by the presence of a serine residue in the active site of the enzyme. The mentioned proteins circulate in a zymogene form and are activated by cleavage of an activation site. There is great homology between all vitamin K-dependent coagulation proteases. Several of them exhibit the increase in activity only assembled in a complex consisting of the protease, cofactors and phosphlipid membranes. The molecular effect of cofactor binding and binding sites are similar among these proteins. The latter substrate-dependent activity of F.IXa modulation is similarly observed for the related coagulation enzymes activated PC (co-factor Protein S), F.Xa (co-factor Factor Va), F.VIIa (cofactor tissue factor), and FIIa (co-factor thrombomodulin), which in the presence of their cofactors, achieve a significant activity or specificity change with their natural substrates substrates. (Hockin et al. 2002).

Thus, a variant of a vitamin K-dependent serine protease of the coagulation cascade is preferably selected from a variant of factor VII (F.VII), factor IX (F.IX), factor X (F.X), protein C or thrombin.

The term "variants" preferably refers to amino acid substitution, addition (insertion) or deletion variants or derivatives of the naturally occurring protein. Variants comprise furthermore an amino acid sequence comprising modified amino acid(s), unnatural amino acid(s) or peptidomimetic(s) or further compounds which can mimic a peptide backbone/structure. Variants can also comprise the substitution or coupling with parts of other molecules or coupling with other molecules.

Amino acid substitutions comprise conservative as well as non conservative replacement by other amino acids or by isosteres (modified amino acids that bear close structural and spatial similarity to protein amino acids), amino acid additions or isostere additions.

Conservative amino acid substitutions typically relate to substitutions among amino acids of the same class. These classes include, for example,
- amino acids having uncharged polar side chains, such as asparagine, glutamine, serine, threonine and tyrosine;
- amino acids having basic side chains, such as lysine, arginine, and histidine;
- amino acids having acidic side chains, such as aspartic acid and glutamic acid; and
- amino acids having nonpolar side chains, such as glycine, alanine, valine, leucine, isoleucine, proline, phenylalanine, methionine, tryptophan, and cysteine.

Variant Proteins of Factor IX

In a preferred embodiment of the present invention a variant of the vitamin K-dependent serine protease factor IX (F.IX) or activated factor XI (F.IXa) is provided, wherein the variant of F.IX is characterized in that it has clotting activity in absence of its cofactor, wherein the cofactor is factor VIII (F.VIII) or activated factor VIII (F.VIIIa).

Factor IX (F.IX) within this patent application refers to the human F.IX protein and cDNA described by Kurachi and Davie, 1982.
Refseq NM_000133 for mRNA/cDNA (SEQ ID NO. 1), and
Refseq NP_000124 for protein sequence (SEQ ID NO. 2).

The amino acid sequence of SEQ ID NO. 2 contains the signal peptide and the pro-peptide of F.IX. The actual numbering starts at −46(Met); +1 is Tyr.

There are several naturally occurring polymorphisms in the gene as well as the amino acid sequence of F. IX. A list from the Hemophilia B Mutation Database, King's College London is shown below. For example, the most frequent polymorphism is at position 147 where threonine can be found in 67% and alanine in 33% of the population. Interestingly, the less frequent alanine is present in the only available recombinant F. IX therapeutic.

| Name | Nuc No | Base Change | AA_Change | Frequency |
|---|---|---|---|---|
|  | −1186 | C→T |  | 52% |
|  | −793 | G→A |  | 44% |
| MseI | −698 | C→T |  | 44% |
| BamHI(i) | −561 | T→G |  | 6% |
|  | 25 | A→G |  | Reported once |
|  | 37 | G→A | −44, R→H | Reported once |
|  | 48 | A→T | −40, I→F | Reported once |

| Name | Nuc No | Base Change | AA_Change | Frequency |
|---|---|---|---|---|
|  | 181 | C→A |  | rare |
|  | 192 | A→G |  | 19% |
|  | 353 | C→T |  | rare |
|  | 709 | A→G |  | rare |
|  | 1778 | C→T |  | 3/10 |
|  | 2627 | T→C |  | 6/10 |
|  | 3747 | C→A |  | 6/10 |
|  | 3756 | T→C |  | 6/10 |
| TaqI(iii) | 3797 | C→T |  | 6/10 |
|  | 3905 | A→T |  | 6/10 |
| DdeI | 5505 | −50 |  | 76% |
|  | 6550 | G→C |  | Reported once |
|  | 6575 | C→G |  | polymorphic in Brazil |
| Pointe-a-Pitre (Guadeloupe) | 6596 | G→T |  | Reported once |
| XmnI | 7076 | G→ |  | 71% |
| TaqI(ii) | 9731 | ? |  | Reported once |
|  | 10512 | A→G |  | Reported 5 times |
| TaqI(i) | 11111 | T→ |  | 65% |
|  | 13275 | C→T |  | 1/10 |
| MspI | 15625 | A→G |  | 78% |
|  | 17397 | T→G |  | 1/10 |
|  | 20002 | C→A |  | 4/10 |
| MnlI (Malmo) | 20421 | G→A | 147, A→T | 33% |
|  | 20512 | T→C | 178, F→L | Reported once |
|  | 27731 | C→G |  | 5/10 |
|  | 28364 | T→C |  | rare |
|  | 29335 | G→A |  | 1/10 |
|  | 29497 | G→T |  | 1/10 |
|  | 29509 | T→C |  | rare |
|  | 29532 | C→T |  | 4/10 |
|  | 29648 | G→A |  | 4/10 |
|  | 29650 | A→G |  | rare |
|  | 30134 | T→C | 227, V→V | Reported 7 times |
|  | 30802 | +A |  | Reported 4 times |
|  | 30890 | C→T | 257, H→Y | Reported 3 times |
|  | 31012 | C→T | 297, N→N | Reported once |
|  | 31093 | G→A | 324, Q→Q | Reported once |
|  | 31103 | G→A | 328, V→I | Reported once |
|  | 32770 | T→C |  | 19% |
|  | 32847 | T→C |  | "c" allele frequent; "t" allele seen 4 times |

Activated factor IX (F.IXa) within this patent application refers to the activated F.IX molecule through cleavage of the 35 amino acid activation peptide as described above.

Since both coagulation factors F.IX and F.VIII always have to be activated before they can exhibit their function both F.IX/F.IXa or F.VIII/F.VIIIa can be used as synonyms.

For the numbering of the amino acid residues the F.IX numbering system is used (according to Kurachi and Davie, 1982, except when indicated otherwise. By some authors in the art, the chymotrypsinogen numbering is used for the description of certain amino acids in homology to the serine protease chymotrypsin. For the present invention the chymotrypsin numbering is only used when explicitly indicated herein.

The "clotting activity" or "functional activity" of F.IX can also be referred to as specific F.IX activity, which is usually measured in Unit/milligram (U/mg). Since one Unit (1 U) of F.IX is referred to as the amount of F.IX in 1 milliliter (ml) of normal human plasma, which corresponds to 5000 ng F.IX, the usual specific activity is around 200 U/mg. Since the specific activity of F.IX is defined as protease activity in the plasma in presence of F.VIII, there is no definition in use in the art for (clotting) activity in absence of cofactor F.VIII. Therefore, the clotting activity in absence of F.VIII, also called "F.VIII-like activity", is expressed herein as percentage of the activity, which an equal amount of wild type F.IX would exhibit in the presence of F.VIII.

Thus, a F.IX variant has "clotting activity" in absence of its cofactor, when it corrects the blood coagulation deficiency caused by the absence of clotting F.VIII in the blood, which in case of a disease can either be due to absence of the F.VIII protein, presence of a defective F.VIII protein, or inhibition of the F.VIII protein, for example by inhibitory antibodies.

The assay system used in the present invention for determining "clotting activity" or "functional activity" of the variants of a vitamin K-dependent serine protease of the coagulation cascade, preferably of F.IX variants, is an one stage assay based on the aPTT. The activated partial thromboplastin time (aPTT or APTT) is a performance indicator measuring the efficacy of both the "intrinsic" (now referred to as the contact activation pathway) and the common coagulation pathways. Apart from detecting abnormalities in blood clotting, it is also used to monitor the treatment effects with heparin, a major anticoagulant. For the determination of the F.VIII or F.IX activity levels in a sample, the test is performed by spiking the sample into F.VIII or F.IX deficient plasma for measurement of the F.VIII or F.IX activity, respectively. This test is referred to as F.VIII or F.IX one stage assay. Now, F.VIII independent activity of a FAX variant can be determined by one stage assay and using F.VIII deficient plasma.

Briefly, blood is collected with oxalate or citrate which arrest coagulation by binding calcium. The plasma is separated from the corpuscular parts of the blood by centrifugation. In the case of recombinantly expressed and purified proteins, the protein is diluted in imidazole buffer. The sample is mixed and added to standardized factor (VIII or IX) deficient plama. In order to activate the intrinsic pathway, phospholipid, an activator (such as silica, celite, kaolin, ellagic acid), and calcium (to reverse the anticoagulant effect of the oxalate) are mixed into the plasma sample. The time is measured until a thrombus (clot) forms. The test is termed "partial" due to the absence of tissue factor from the reaction mixture (see Langdell et al., 1953).

Preferably, the variants of faxtor IX according to the invention have clinical relevant clotting activity (or clotting activity with clinical relevance), i.e. clotting activity which makes the variants suitable for clinical applications, as disclosed herein below.

A preferred clotting activity with clinical relevance is 1% or more clotting activity of the variant in absence of cofactor F.VIII, wherein 100% refers to the activity of wild type F.IX in presence of cofactor F.VIII or F.VIIIa.

Around 1% sustained factor VIII or factor IX levels are enough in prophylactic treatment regimens to prevent major bleeding complications in severe hemophilia patients. To reach a 1% level in a severe hemophilia A patient with a factor IX variant which has "1% F.VIII-like" activity in absence of F.VIII, F.IX variant levels of 100% of normal (around 5000 ng/ml) additional to the already physiologically present F.IX would be necessary. Such a treatment seems feasible and therefore the clinically relevant "factor VIII-like" activity is estimated at 1%.

In an embodiment the variant factor IX of the invention comprises a modification of the 99-loop, preferably by amino acid substitutions, insertions and/or deletions. A modification of the 99-loop can also be achieved by affecting the loop structure by amino acid substitutions, insertions and/or deletions of adjacent amino acid residues or residues interacting otherwise with the 99-loop.

The 99-loop or insertion loop 80-90 (according to chymotrypsinogen numbering) of factor IX encompasses amino acid residues 256 to 268 (F.IX numbering). The 99-loop is positioned near the active site and plays a role in the activation of F.IX. According to Sichler et al. (2003), Tyr-177 locks the 99-loop in an inactive conformation which, in the physiologic complex, is released by cofactor F.VIIIa. F.X is then able to rearrange the unlocked 99-loop and subsequently binds to the active site cleft.

The variant factor IX according to the invention comprises preferably at least one amino acid substitution in a position selected from the group of 265, 4, 338, 377, 259, 345, 1, 10, 37, 50, 85, 116, 119, 120, 181, 217, 235, 245, 253, 259, 301, 360, 383, 340, 86, 25, 34, 290, 291, 274, 353, 358, 375, 388, 35, preferably K265T, G4Y, R338A, S377W, Y259F, Y345T, Y1A, V10K, R37T, Q50P, D85A, R116A, R119A, N120A, V181I, V217L, E235K, E245V, V253I, Y259F, K301I, S360A, I383V, T340S, V86A, F25Y, N34D, I290L, A291P, E274K, F353Y, R358A, G375F, E388G, T35D, and/or a modification of the 99-loop, or preferably 265, 4, 338, 377, 259, 345, 1, 10, 37, 50, 85, 116, 119, 120, 181, 217, 235, 245, 253, 259, 301, 360, 383, 340, 86, 25, 34, 290, 291, 274, 353, 358, 375, 388, 35, 277, or preferably K265T, K265A, G4Y, R338A, R338L, S377W, Y259F, Y345T, Y1A, V10K, R37T, Q50P, D85A, R116A, R119A, N120A, V181I, V217L, E277A, E235K, E245V, V253I, Y259F, K301I, S360A, I383V, T340S, V86A, F25Y, N34D, I290L, A291P, E274K, F353Y, R358A, G375F, E388G, T35D, and/or a modification of the 99-loop.

Preferably, the variant factor IX according to the invention comprises at least one amino acid substitution in a position selected from the group of 255 to 269, 383, 181, 290, 388, 34, 25, 353, 358, 338, 377, 4, 86, 217, 277, and/or a modification of the 99-loop.

More preferably, the variant factor IX comprises at least an amino acid substitution selected from K265T, I383V, V181I, I290L, E388G, N34D, F25Y, F353Y, R358A, R338A, R338L, S377W, G4Y, V86A, V217L, E277A and/or a modification of the 99-loop.

In a preferred embodiment, the variant factor IX comprises an amino acid substitution in position 265 (position 98 according to chymotrypsinogen numbering), preferably K265T (K98T according to chymotrypsinogen numbering) or, preferably, an amino acid substitution in position 265 which is selected from K265T, K265A, K265G, K265V, K265N and K265D.

In a preferred embodiment, the variant factor IX comprises an amino acid substitution in position 265 (preferably selected from K265T, K265A, K265G, K265V, K265N and K265D) or the amino acid substitution K265T (K98T according to chymotrypsinogen numbering) in combination with a further amino acid substitution.

The further amino acid substitution is preferably an (more preferably at least one) amino acid substitution in a position selected from the group of 4, 338, 377, 259, 345, 1, 10, 37, 50, 85, 116, 119, 120, 181, 217, 235, 245, 253, 259, 301, 360, 383, 340, 86, 25, 34, 290, 291, 274, 353, 358, 375, 388, 35 and/or 277, more preferably selected from the group of:

383, 181, 290, 388, 34, 25, 353, 358, 338, 377, 4, 86, 217 and/or 277.

More preferably, the variant factor IX comprises the amino acid substitution K265T and an amino acid substitution selected from I383V, V181I, I290L, E388G, N34D, F25Y, F353Y, R358A, R338A, R338L, S377W, G4Y, V86A, V217L and/or E277A.

More preferably, the variant factor IX comprises an amino acid substitution in position 265 or the amino acid substitution K265T and (in combination with) an amino acid substitution selected from I383V, V181I, I290L, E388G, N34D, F25Y, F353Y, R358A, R338A, R338L, S377W, G4Y, V86A, V217L and/or E277A.

In a further preferred embodiment of the invention the variant factor IX comprises multiple amino acid substitutions from the group of amino acid positions 265, 4, 338, 377, 259, 345, 1, 10, 37, 50, 85, 116, 119, 120, 181, 217, 235, 245, 253, 259, 301, 360, 383, 340, 86, 25, 34, 290, 291, 274, 353, 358, 375, 388, 35, 277, wherein "multiple amino acid substitutions" refers to substitutions in 2, 3, 4 or more positions.

Basis F.IX Variant (Group A)

The inventors have found a F.IX variant which allows F.VIII-independent therapy of bleeding disorders: a variant with an amino acid substitution in position 265, preferably K265T (K98T according to chymotrypsin numbering). K265T has been described in a different context in Sichler et al. 2003. Kolkman and Mertens (2000) describe a K265A variant.

The mutations/variations of F.IX assessed by the inventors are based on the observation that F.IXa has a poor activity compared to other serine proteases like F.Xa. In fact, exchanging only few amino acids affecting the 99-loop of F.IX by corresponding F.X sequences resulted in a dramatic improvement of amidolytic activity (up to several thousand-fold) in kinetic studies with truncated recombinant F.IXa variants using peptide substrates (see Hopfner et al., 1997 and Sichler et al., 2003)). At the same time a shift in specificity towards a "F.X-like" function was observed. Since these studies model F.IXa in a form not assembled to the intrinsic tenase complex, the inventors hypothesized that a variant protein with the same mutations could enable intrinsic propagation of the clot formation in absence of F.VIII. To test this the inventors introduced the mutations Y259F/K265T/Y345T (FTT) into F.IX and expressed the protein in tissue culture. Basically no effect was seen on F.IX specific activity; however the activity in F.VIII-deficient plasma increased dramatically.

Kolkman and Mertens (2000) already mentioned that a variant 1(265A could increase F.VIII-independent F.IX activity by a factor of 20. However, the tested F.IX Y259F/K265T/Y345T resulted in 2% activity at normal (100%) antigen levels in absence of F.VIII (FIG. 2). Considering that the presence of F.VIII increases F.IX activity by a factor of $10^6$, the triple mutant resulted in an 20,000-fold increase in F.VIII-independent activity. This puts the clotting activity of the variant in absence of F.VIII in a range, in which this would also have physiological importance at the moment of clot formation or as possible therapeutic. Since this activity is still a small fraction of the F.IX-specific activity in presence of F.VIII (100% of F.IX antigen corresponds to 2% of "F.VIII-like" activity, i.e. "clotting activity in absence of cofactor F.VIII"), the inventors included additional mutations chosen by structural properties and homology comparisons of other serine proteases. They further tested the mutations Y259F, K265T, and Y345T independent from each other and could identify a single amino acid mutation (K265T, i.e. K98T in chymotrypsin numbering) which resulted in an enzyme with 191% F.IX and 6.7% "F.VIII-like" clotting activity and determined that the other single mutations are only decreasing the protease activity in presence and absence of F.VIII. (see Table 1)

Thus, in a preferred embodiment the variant factor IX is characterized that it has clotting activity in absence of cofactor F.VIII and has the K265T amino acid substitution.

The inventors have shown that position 265 is the main determinant for F.VIII bypassing activity of F.IX variants. The inventors showed that reversing residue 265 from T to the natural occurring K (V181I/265K/I383V, IKV) resulted in a near complete loss of F.VIII independent activity. Surprisingly, other amino acid substitutions, especially in the variants K265A/V181I/I383V, K265G/V181I/I383V, K265N/V181I/I383V, K265N/V181I/I383V, or K265D/V181I/I383V, resulted in similar F.VIII-bypassing activity than K265T/V181I/I383V, being highest for K265A/V181I/I383V. This result was unexpected, since the F.VIII independent activity for a factor IX variant carrying the single K265A substitution which was previously described was in a far lower range (Kolkman and Mertens, 2000).

Therefore, in a further preferred embodiment, the variant factor IX is characterized that it has clotting activity in absence of cofactor F.VIII and has an amino acid substitution in position 265, preferably selected from K265T, K265A, K265G, 1(265V, K265N and K265D or other amino acids.

However, the present invention does not encompass a variant factor IX that only has the amino acid substitution K265A. According to the present invention, if amino acid substitution K265A is present in a variant factor IX this implies that the variant has further amino acid substitutions in combination with K265A, i.e. it comprises further amino acid substitutions, such as in positions 181 and/or 383.

The inventors have furthermore found that the protein activity of F.IX can be even further modified by introduction of additional amino acid substitution to the amino acid substitution of Group A in order to obtain a F.IX variant with desired properties:

| | Amino acid position | Amino acid substitution |
| --- | --- | --- |
| Group A | 265 | K265T or other amino acid substitution (preferably selected from K265T, K265A, K265G, K265V, K265N and K265D) but not K265A alone |
| Group B | 383, 181, 290 | I383V, V181I, I290L |
| Group C | 388, 34, 25, 353, 358, 383 | E388G, N34D, F25Y, F353Y, R358A, I383V |
| Group D | 338, 377, 4, 86, 217, 277 | R338A, R338L, S377W, G4Y, V86A, V217L, E277A |

Modification of the preferred amino acid positions above (e.g. by amino acid substitution) can be combined with each other, preferably in the following way. However, further combinations are possible.

Group A alone—clotting activity in absence of cofactor F.VIII (F.VIII-independent activity) increased compared to wild type Group D alone—increased clotting activity in presence of cofactor F.VIII (F.VIII-dependent activity) increased compared to wild type Group A+B—clotting activity in absence of cofactor F.VIII wherein the F.VIII-independent clotting activity is increased compared to the respective clotting activity of the basis variant (Group A).

Group A+C—clotting activity in absence of cofactor F.VIII and decreased activity in presence of cofactor F wherein the F.VIII-dependent activity is decreased compared to wild type and preferably to the respective activity of the basis variant (Group A).

Group A+B+C—clotting activity in absence of cofactor F.VIII and decreased clotting activity in presence of cofactor F.VIII
wherein the F.VIII-independent clotting activity is increased compared to the respective clotting activity of the basis variant (Group A) and
wherein the F.VIII-dependent activity is decreased compared to wild type and preferably to the respective activity of the basis variant (Group A).

Group A+D—clotting activity in absence of cofactor and increased clotting activity in presence of cofactor
wherein the F.VIII-dependent activity which is increased compared to wild type and preferably to the respective activity of the basis variant (Group A).

Group A+B+D—clotting activity in absence of cofactor and increased clotting activity in presence of cofactor
wherein the F.VIII-independent clotting activity is increased compared to the respective clotting activity of the basis variant (Group A)
wherein the F.VIII-dependent activity which is increased compared to wild type and preferably to the respective activity of the basis variant (Group A).

With the intention to generate F.IX variants with highest possible activity in absence of F.VIII, the inventors further added two additional amino acid substitutions (Group B), resulting in a protein (V181I/K265T/I383V) with 167% F.IX and 16% "F.VIII like" activity. The variant accordingly has a 160,000-fold higher clotting activity in absence of F.VIII compared to the wild type protein. These additional amino acid substitutions were chosen in a way to maximally increase F.VIII independent F.IX activity without exorbitantly increasing the F.IX specific activity. The rationale behind this approach was that too much F.IX specific activity in presence of F.VIII might increase the risk of thrombotic complications and therefore pose a concern for using the proposed F.IX variants as therapeutic. Also other combinations of the above listed amino acid substitutions are possible, for example amino acid substitutions from Group C can further restrict the activity of a variant protein in presence of F.VIII while only minimally affecting the activity in absence of F.VIII. Similarly, the activity in both, presence and absence of F.VIII, can be improved using amino acid substitutions from Group D. In this way a variant with the five mutations V181I/K265T/R338A/S377W/I383V was generated which exhibits increased activity in absence of F.VIII (22% "F.VIII like" activity corresponding to 220,000-fold higher then wild type F.IX) and in presence of F.VIII (16-fold higher compared to wild type F.IX). The FIX and "FVIII like" activities of tested variants are illustrated in Table 1.

The possibility of these further modifications is important since it allows the design and tailoring of F.IX variants for specific applications, such as (1) Low F.IX activity in presence of F.VIII (F.VIII-dependent activity) while high F.IX activity in absence of F.VIII (F.VIII-independent activity) (i.e. Groups A+C) is desired to decrease thrombogenicity of a therapeutic to treat hemophilia A or patients with inhibitory antibodies against F.VIII.

(2) A protein with high protease activity independently of presence of F.VIII or F.IX might have the potential to treat all types of F.IX or F.VIII deficiencies ((i.e. Group A+B+D).

Since the effects of the listed single amino acid substitutions is of differentiated strength with respect to their effect on F.IX activity in absence or presence of F.VIII, also amino acid substitutions from different Groups can be combined to achieve a desired over all effect on F.IX activity for specific applications. For example, combining the 1(265T variant (Group A) with the amino acid substitutions V181I and I383V (Group B), results in a protein with high activity in absence of F.VIII, but basically normal activity in presence of F.VIII, corresponding to application (1). For details please see Table 1.

All variants of Group A and in combination of Group A are especially suitable for the therapy of patients with hemophilia A, inhibitory antibodies and other bleeding disorders as well as for the treatment of hemophilia B.

In more detail:

FIX variants which in combination with the basis variant further increase clotting activity in absence of F. VIII (Group A combined with Group B)

In this preferred embodiment of the invention, a variant factor IX is characterized in that it has clotting activity in absence of cofactor F.VIII, and comprises at least one amino acid substitution in a position selected from the group of 265, 383, 181 and 290.

Preferably, the variant factor IX comprises the amino acid substitution K265T and amino acid substitution(s) in a position selected from the group of 383, 181 and/or 290 (group B), more preferably comprises the amino acid substitution K265T and amino acid substitution(s) selected from I383V, V181I and/or I290L.

Preferably, the variant factor IX comprises an amino acid substitution in position 265 or the amino acid substitution K265T, in combination with amino acid substitution(s) in a position selected from the group of 383, 181 and/or 290 (group B), more preferably comprises an amino acid substitution in position 265 or the amino acid substitution K265T and amino acid substitution(s) selected from I383V, V181I and/or I290L.

An amino acid substitution in position 265 is preferably selected from K265T, K265A, K265G, K265V, K265N and K265D.

These F.IX variants of Group A+B have a F.VIII-independent clotting activity which is increased compared to the respective clotting activity of the basis variant (Group A).

FIX variants which in combination with the basis variant restrict the clotting activity in presence of F. VIII (Group A combined with Group C)

In this preferred embodiment of the invention, a variant factor IX is characterized in that it has clotting activity in absence of cofactor F.VIII, but decreased activity in presence of cofactor F.VIII, and comprises at least one amino acid substitution in a position selected from the group of 265, 383, 388, 34, 25, 353 and/or 358.

Preferably, the variant factor IX comprises the amino acid substitution K265T and amino acid substitution(s) in a position selected from the group of 388, 34, 25, 383, 353 and/or 358 (Group C), more preferably comprises the amino acid substitution K265T and amino acid substitution(s) selected from E388G, N34D, F25Y, F353Y, I383V and/or R358A.

These F.IX variants of Group A+C have a F.VIII-dependent activity which is decreased compared to wild type and preferably to the respective activity of the basis variant (Group A) (or preferably decreased compared to variant(s) of Group A+B). Thus, these F.IX variants of Group A+C restrict F.VIII-dependent activity and minimize possible thrombogenic risks.

FIX variants which in combination with the basis variant further increase clotting activity in absence of F. VIII as well as restrict the clotting activity in presence of F. VIII (Group A combined with Group B and Group C)

In this preferred embodiment of the invention, a variant factor IX is characterized in that it has clotting activity in absence of cofactor F.VIII, but decreased activity in presence of cofactor F.VIII and comprises at least one amino acid substitution in a position selected from the group of 265, 383, 181, 290, 388, 34, 25, 353 and/or 358, Preferably, the variant factor IX comprises the amino acid substitution K265T and amino acid substitution(s) in a position selected from the group of 383, 181, 290, 388, 34, 25, 353 and/or 358 (group B+C), more preferably comprises the amino acid substitution K265T and amino acid substitution(s) selected from I383V, V181I, I290L, E388G, N34D, F25Y, F353Y and/or R358A.

These F.IX variants of Group A+B+C combine the characteristics of the three groups:

they have F.VIII-independent clotting activity, they have a F.VIII-independent clotting activity which is increased compared to the respective clotting activity of the basis variant (Group A) and they have a F.VIII-dependent activity which is decreased compared to wild type and preferably to the respective activity of the basis variant (Group A) (or preferably decreased compared to variant(s) of Group A+B).

Thus, these F.IX variants of Group A+B+C increase F.VIII-independent activity, restrict F.VIII-dependent activity and minimize possible thrombogenic risks.

Variant proteins of factor IX with increased clotting activity in presence of cofactor F. VIII (Group D)

In a further aspect of the present invention, a variant of factor IX (F.IX) is characterized in that it has increased clotting activity in presence of its cofactor compared to wild type, wherein the cofactor is factor VIII (F.VIII) or activated factor VIII (F.VIIIa).

A variant factor IX according to this aspect of the present invention comprises at least one amino acid substitution in a position selected from the group of 338, 377, 4, 86, 217 and/or 277, more preferably comprises at least one amino acid substitution selected from R338A, R338L, S377W, G4Y, V86A, V217L and/or E277A.

The variants of Group D and variants that are combined with Group D are especially suitable for the treatment of hemophilia B.

A protein with isolated high F.IX activity in presence of F.VIII is a good therapeutic for the treatment of F.IX deficiency. For this purpose, no high activity in absence of F.VIII, i.e. Group A, such as mutation K265T, is required. The amino acid subsitutions of Group D also increase F.IX activity in presence of F.VIII in absence of the above mentioned K265T mutation (Group A). A list of variants tested for this purpose without introduction of the K265T mutation are shown in Table 2.

Variant proteins of factor IX with clotting activity in absence of cofactor and increased clotting activity in presence of cofactor (Group A combined with Group D)

In this preferred embodiment of the invention, a variant factor IX is characterized in that it has clotting activity in absence of cofactor F.VIII and increased clotting activity in presence of cofactor F.VIII compared to wildtype, and comprises at least one amino acid substitution in a position selected from the group of 265, 338, 377, 4, 86, 217 and/or 277.

Preferably, the variant factor IX comprises the amino acid substitution K265T and amino acid substitution(s) in a position selected from the group of 338, 377, 4, 86, 217 and/or 277 (group D), more preferably comprises the amino acid substitution K265T and amino acid substitution(s) selected from R338A, R338L, S377W, G4Y, V86A, V217L and/or E277A.

These F.IX variants of Group A+D have a F.VIII-dependent clotting activity which is increased compared to the respective F.VIII-dependent clotting activity of wild type, and preferably of the basis variant (Group A). They have also an increased potency for treatment of hemophilia B.

Variant proteins of factor IX with increased clotting activity in absence as well as in presence of cofactor (Group A combined with Group B and Group D)

In this preferred embodiment of the invention, a variant factor IX is characterized in that it has (increased) clotting activity in absence of cofactor F.VIII and increased clotting activity in presence of cofactor F.VIII, and comprises at least one amino acid substitution in a position selected from the group of 265, 383, 181, 290, 338, 377, 4, 86, 217 and/or 277.

Preferably, the variant factor IX comprises the amino acid substitution K265T and amino acid substitution(s) in a position selected from the group of 383, 181, 290, 338, 377, 4, 86, 217 and/or 277, more preferably comprises the amino acid substitution K265T and amino acid substitution(s) selected from I383V, V181I, I290L, R338A, R338L, S377W, G4Y, V86A, V217L and/or E277A.

These F.IX variants of Group A+B+D combine the characteristics of the three groups:

they have F.VIII-independent clotting activity, they have a F.VIII-independent clotting activity which is increased compared to the respective clotting activity of the basis variant (Group A) and they have a F.VIII-dependent activity which is increased compared to wild type and preferably to the respective activity of the basis variant.

The variant factor IX according to the invention is more preferably selected from variant K265T,
variant K265T/V181I,
variant K265T/I383V,
variant K265T/V181I/I383V,
variant K265T/V181I/I383V/R338A/S377W,
variant K265T/V181I/I383V/E388G,
variant K265T/V181I/I290L/I383V,
variant K265T/V181I/I290L/I383V/E388G,
variants comprising R338A and S377W.

More preferably, the variant factor IX according to the invention is variant K265T,
variant K265T/V181I,
variant K265T/I383V,
variant K265T/V181I/I383V, or
variant K265T/V181I/I383V/R338A/S377W.

In a preferred embodiment, the variant factor IX according to the invention is selected from variant K265T or a variant with an amino acid substitution in position 265 (preferably selected from K265T, K265A, K265G, K265V, K265N and K265D), preferably in combination with an amino acid substitution in position 181 and/or 383 (preferably V181I and/or I383V), More preferably, the variant factor IX according to the invention is
variant K265T/V181I/I383V,
variant K265A/V181I/I383V,
variant K265G/V181I/I383V,
variant K265V/V181I/I383V,
variant K265N/V181I/I383V, or
variant K265D/V181I/I383V.

The expression, for example, "K265T/V181I/I383V" refers to a variant containing these amino acid substitutions in combination, i.e. K265T and V181I and I383V in combination. The expression "K265T/V181I/I383V/R338A/S377W" refers to a variant containing these amino acid substitutions in combination, i.e. K265T and V181I and I383V and R338A and S377W in combination, and so one.

Disclaimer:

The present invention does not encompass a variant factor IX that only has the amino acid substitution K265A. According to the present invention, if amino acid substitution K265A is present in a variant factor IX this implies that the variant has further amino acid substitutions in combination with K265A, i.e. it comprises further amino acid substitutions, such as in positions 181 and/or 383.

Furthermore, the present invention does not encompass a variant factor IX that only has the following amino acid substitution(s):
FTT (Y259F/K265T/Y345T);
Y259F/K265T;
V181F;
R338A.

Also, the following variants of factor IX are not encompassed by the present invention:
Y259F/A261K/K265T/Y345T
Y259F/K265T/Y345F/I383V/E388G
Y259F/A261K/K265T/Y345F/I383V/E388G Modification of the 99-loop has been attempted repeatedly as strategy to modify F.IX activity (Hopfner et al., 1997, Sichler et al., 2003). The most promising variants Y259F (/A261K) and K265T) have been further investigated for possible activity in absence of F.VIII (Hartmann et al., 2007 as well as WO 2008/092644 and WO 2008/092643). The idea behind this approach was to modify the conformation of the F.IX specific 99-loop by changing residues at both ends of the loop. The surprising finding in our investigation was that in contrast to the F.IX models described, in which F.IX was partially truncated and/or produced in bacteria instead of eukaryotic cells, the F.VIII independent activity solely depends upon mutation at position 265. Further more, the mutation at position Y259F was hindering the F.VIII independent and overall activity and only excluding the mutation at position Y259F high enough F.VIII independent activities could be obtained to further pursue an approach using F.IX variants as therapeutics.

In case of the mutations I383V and E388G, the case was similar. Both mutations were seen as a unit in the first description by Hopfner et al. (1997) and later on by the descriptions from Baxter (see Hartmann et al., 2007 as well as WO 2008/092644 and WO 2008/092643)). Hopfner et al. (1997) even reported that I383V only had a moderate effect in the bacterial F.IX expression system and therefore was propagated only in combination with E388G. Our experiments suggest the contrarian. Only the mutation I383V added to the F.VIII independent F.IX activity, while E388G was disturbing the activity. We believe that these differences are crucial for potential development of a new F.IX based bypassing agent. First of all, the activities necessary to improve hemostasis are improved by several fold excluding these mutations, and secondary, the numbers of mutations introduced into F.IX will be the main safety concern, since the risk of the formation of inhibitory antibodies to F.IX probably would increase with the amount of changes which are introduced into the protein.

Conjugates

In a preferred embodiment, the variants of factor IX according to the invention comprise a further compound or moiety, which is preferably covalently attached to the variant (conjugate).

Preferably, the further compound or moiety is selected from
a protein, such as albumin,
a label, such as chromophor, fluorophor, isotope,
and/or
a polymer, such as PEG.

Nucleic Acids of the F.IX Variants and Pharmaceutical Compositions

According to the present invention the above object is furthermore solved by providing nucleic acids encoding the variant factor IX according to the present invention.

A "nucleic acid" refers to DNA, RNA and derivatives thereof, DNA and/or RNA comprising modified nucleotides/nucleosides.

Preferably, the nucleic acid is operably linked to a promoter and/or terminator sequence. Preferred promoter and/or terminator sequences are the human alpha1 anti-trypsin promoter, the hepatic locus control region 1, or the cytomegalovirus promoter and a polyadenylation signal vom human or bovine growth hormone of the Simianese Virus 40.

The skilled artisan is able to select suitable promoter and/or terminator sequences.

A nucleic acid is "operably linked" to a promoter and/or terminator sequence when the transcription/translation of the nucleic acid is controlled by the respective promoter/terminator, preferably in a cell and by the cellular transcription/translation machinery, such that e.g. the encoded protein can be obtained from the nucleic acid.

Preferably, the nucleic acid is an expression plasmid, a gene therapy construct, a sequence encoded in a gene transfer vector, a gene sequence used for DNA modification or repair, or similar.

Preferred gene therapy constructs are viral and non-viral vectors, such as adeno-associated viral vectors (AAV), plasmid vectors, or minicircle vectors, as described e.g. in (Schuettrumpf et al., 2005).

According to the present invention the object is furthermore solved by providing a pharmaceutical composition comprising at least one variant of factor IX (F.IX) of the invention or at least one nucleic acid of the invention, and optionally pharmaceutically acceptable carrier(s) and/or excipient(s).

Suitable pharmaceutically acceptable carrier(s) and/or excipient(s) are known in the art. The skilled artisan will selected the preferred pharmaceutically acceptable carrier(s) and/or excipient(s) depending on the intended application of the pharmaceutical composition, such as disorder to be treated, patient to be treated, treatment regimen etc.

Medical Uses

According to the present invention the object is furthermore solved by providing the variants of a vitamin K-dependent serine protease of the coagulation cascade, most preferably the variants of factor IX, as disclosed in the present invention or the nucleic acids encoding them or the pharmaceutical compositions of the invention for the diagnosis, prevention and/or treatment of diseases.

The disease to be diagnosed, prevented and or treated is preferably a bleeding disorder or bleeding.

A "bleeding disorder" is preferably hemophilia A and/or hemophilia B, hemophilia caused or complicated by inhibitory antibodies to factor VIII, by a deficiency of factor VIII or factor IX, or by the presence of a non functional factor VIII or factor IX protein, or any other bleeding or bleeding tendency.

Preferably, the bleeding disorder is hemophilia A, hemophilia caused or complicated by inhibitory antibodies to factor F.VIII or F.VIIIa, hemophilia B.

Preferably, the bleeding disorder or bleeding is a bleeding disorder where by-passing agents are used, including e.g. neonatal coagulopathies; severe hepatic disease; high-risk surgical procedures; traumatic blood loss; bone marrow transplantation; thrombocytopenias and platelet function disorders; urgent reversal of oral anticoagulation; congenital deficiencies of factors V, VII, X, and XI; and von Willebrand disease with inhibitors to von Willebrand factor, blood loss in connection with large injuries, cerebral bleedings, thrombocyte function disorders.

According to the present invention the object is furthermore solved by using a variant of a vitamin K-dependent serine protease of the coagulation cascade, most preferably the variants of factor IX, as disclosed in the present invention or the nucleic acids encoding them for the manufacture of a medicament for the treatment and/or the prevention of a bleeding disorder or bleeding.

Preferably, the variant of factor IX (F.IX), the nucleic acid or the pharmaceutical composition of the invention are used for protein infusion therapy, cellular therapy, gene therapy and/or prophylaxis of a bleeding disorder or bleeding.

Diagnosis, prevention and/or treatment, wherein the disease is hemophilia A or hemophilia caused or complicated by inhibitory antibodies to factor F.VIII or F.VIIIa: preferably by
  a variant of Group A, more preferably variant K265T
  variants of Group A in combination with Group B and/or C and/or D
    Group A+B as defined herein
    Group A+C as defined herein
    Group A+B+C as defined herein
    Group A+D as defined herein
    Group A+B+D as defined herein
  the respective nucleic acids, pharmaceutical compositions.

The inventors are the first to apply a variant of Group A, in particular K265T, for the treatment of hemophilia A or hemophilia caused or complicated by inhibitory antibodies to factor F.VIII or F.VIIIa.

The variant F.IX molecules with higher protease/clotting activity in absence of F.VIII could be an alternative to common bypassing agents, with the advantage of being activated directly at the site of injury. This would resemble physiologic clot formation, prevent the infusion of already activated proteases as usual in the available bypassing agents at the moment, and make therapy safer.

A zymogene F.IX variant would presumably also have a far longer half life, enabling prophylactic substitution therapy also in inhibitor patients. Intriguingly, patients lacking F.VIII could even be suitable for a gene transfer approach using the smaller and less immunogenic F.IX, for which gene therapy studies are far more promising at the moment. Thinking of the relatively small number of patients and the large efforts necessary bringing gene therapy for hemophilia into clinical praxis, the proposed F.IX variants could even bundle the efforts offering therapy for patients with hemophilia A and hemophilia B, or with inhibitory antibodies to F.VIII. Eventually, the variant would also be useful in the treatment of other bleeding disorders.

Another aspect of the described variants is, that without need for F.VIIIa and higher activity towards both, F.X cleavage and chromogenic substrate cleavage, the variants could be used in diagnostic testing systems or for the development and screening for direct F.IXa inhibitory substances, which since a long time are desired as anticoagulants, but for which no effective screening was possible, due to the low efficacy of F.IXa without assembly in the tenase complex.

Diagnosis, prevention and/or treatment, wherein the disease is hemophilia B, by all variants described herein preferably by
  a variant of Group A, more preferably variant K265T
  variants of Group A in combination with Group B and/or C and/or D
    Group A+B as defined herein
    Group A+C as defined herein
    Group A+B+C as defined herein
    Group A+D as defined herein
    Group A+B+D as defined herein
  a variant of Group D, more preferably variant K265T
  variants of Group D in combination with Group A and/or B
    Group A+D as defined herein
    Group A+B+D as defined herein
  the respective nucleic acids, pharmaceutical compositions.

Diagnosis, prevention and/or treatment of a bleeding disorder or bleeding, wherein furthermore the thrombogenic risks are minimized preferably by
  variants in combination with Group C
    Group A+C as defined herein
    Group A+B+C as defined herein
  the respective nucleic acids, pharmaceutical compositions.

Diagnosis, prevention and/or treatment of both, hemophilia A and B by all variants described herein except Group D alone.

Diagnosis, prevention and/or treatment of hemophilia A or hemophilia caused or complicated by inhibitory antibodies to factor F.VIII as well as hemophilia B, by all variants described herein except Group D alone.

The variants of the present invention are suitable tools to treat patients with bleeding disorder using protein administration, or cell- or gene therapeutic administration (viral, DNA, RNA, or other vectors). Diseases for treatment are hemophilia A and B, also caused or complicated by inhibitory antibodies to FVIII, for treatment of bleeding and for prophylactic therapy.

The inventors have shown that the variants of the present invention
  correct clotting time in presence of inhibitory antibodies against F.VIII (confirming the function of the tested F.IX variants also in presence of high titers of F.VIII inhibitors),
  correct coagulation in vivo (being the first evidence that F.IX variants can serve as hemostatically active therapeutics in vivo),
  stop bleeding in presence of inhibitory antibodies against F.VIII (confirming the functionality of F.IX variants in both, in presence and in absence, of inhibitory antibodies to F.VIII).

For further details, see Examples 6-8 and FIGS. 4-7.

Screening Method

According to the present invention, the object is furthermore solved by providing a method for screening of anticoagulant compounds (anticoagulants), preferably substances that directly inhibit F.IXa.

Such a method comprises the use of at least one variant factor IX of the present invention, as defined herein.

In such a method, no further components of the tenase complex are necessary (wherein "tenase" refers to complex of the activated forms of the blood coagulation factors factor VIII (F.VIIIa) and factor IX (F.IXa). It forms on a phospholipid surface in the presence of calcium and is responsible for the activation of factor X).

An advantageous aspect of the described variants is, that without need for F.VIIIa and higher activity towards both, F.X cleavage and chromogenic substrate cleavage, the variants are suitable tools in diagnostic testing systems or for the development and screening for direct F.IXa inhibitory substances, which since a long time are desired as anticoagulants, but for which no effective screening was possible, due to the low efficacy of F.IXa without assembly in the tenase complex.

A screening method according to the invention is preferably a method for identifying a compound which binds to a variant factor IX of the present invention and/or which modulates its activity,
  preferably comprising the following steps:
  providing compounds/substances to be tested,
  providing at least one variant factor IX of the present invention,
  contacting a compound/substance to be tested with the at least one variant factor IX of the present invention,
  determining whether the compound/substance binds to the at least one variant factor IX,
  optionally, determining whether the compound/substance modulates the activity of the at least one variant factor IX.

The following examples and drawings illustrate the present invention without, however, limiting the same thereto.

BRIEF DESCRIPTION OF THE DRAWINGS

FIG. 1 Factor IX amino acid and nucleotide sequence sequences.

The mutations introduced are highlighted.

Figure 2:
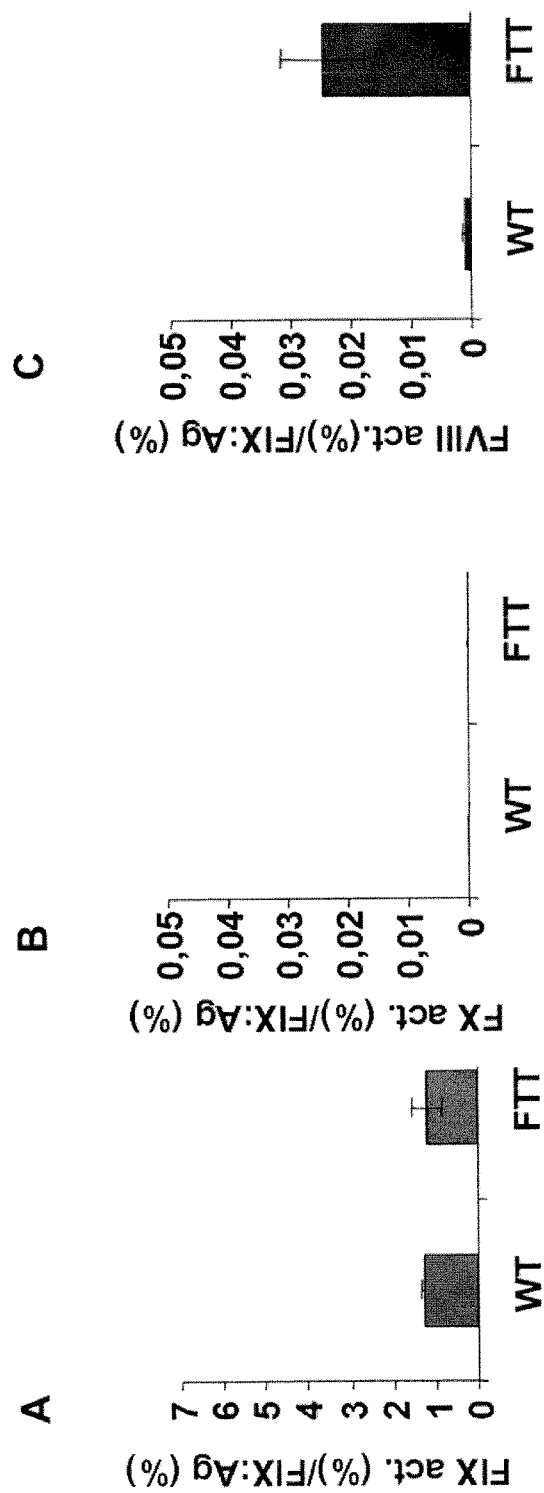

FIG. 2 Clotting activity of wildtype factor IX (WT) or FIX variant containing the FFT substitutions (FFT) in F.IX-, F.X-, and F.VIII-deficient plasma.
  (A) F.IX-deficient plasma.
  (B) F.X-deficient plasma.
  (C) F.VIII-deficient plasma.

Values represent activity (%) divided by antigen levels of F.IX (%) (+/− standard deviation). As expected WT F.IX has a quotient of 1 when activity was tested in F.IX deficient plasma (see A), but has no activity in F.X- or F.VIII-deficient plasma (see B and C).

The variant containing the FFT substitutions (FTT) shows an activity of 2% in F.VIII-deficient plasma at 100% (5000 ng/ml) F.IX antigen levels (see C), while the activity in F.X-deficient plasma was negligible (see B).

FIG. 3

F.IX expression cassettes for F.IX expression in tissue culture (A) or liver-specific expression in mice (B). Mutations to create F.IX variants were introduced by site directed mutagenesis as highlighted for the K265T amino acid substitution.

Figure 4:
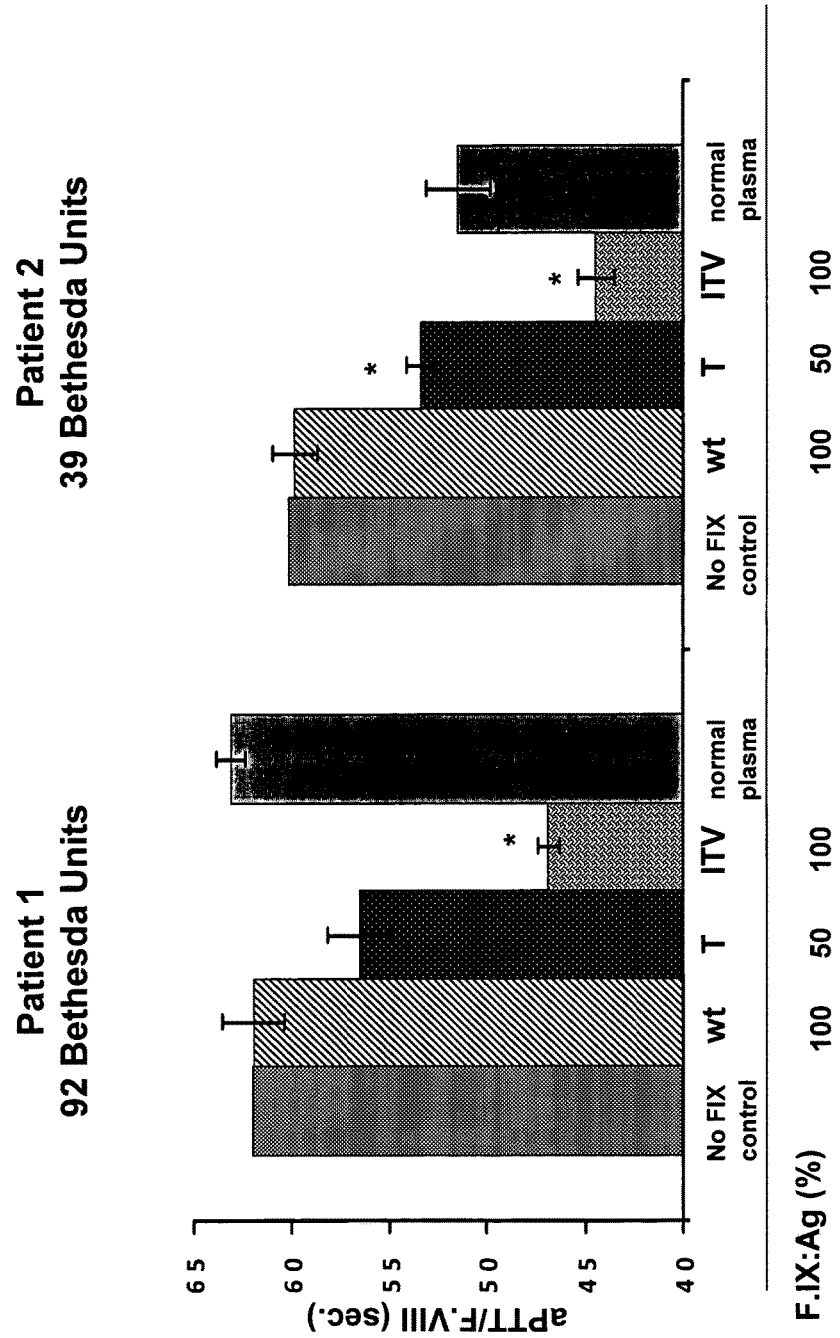

FIG. 4 aPTT-based One Stage F. VIII assay in plasma of patients with an acquired form of hemophilia A caused by high titers of inhibitory antibodies to F.VIII.

Normal control plasma, F.IX WT, or variants K265T (T) or V181I/K265T/I383V (ITV) were mixed into patient plasma at equal volumes (1:1). The mix was incubated at 37° C. for two hours and then clotting activity was determined in F.VIII deficient plasma. While normal control plasma did not or did only insufficiently normalize clotting times, the F.IX variants T and ITV led to a significant shortening of the clotting times at levels of 50% or 100% of normal human F.IX antigen levels, respectively. The observed coagulation function in presence of inhibitory anti-F.VIII antibodies is in good accordance with the previously listed values in F.VIII deficient plasma. The graph shows mean values with standard error of means as error bars. *Student's t-test in comparison to F.IX WT with p<0.05

Figure 5:
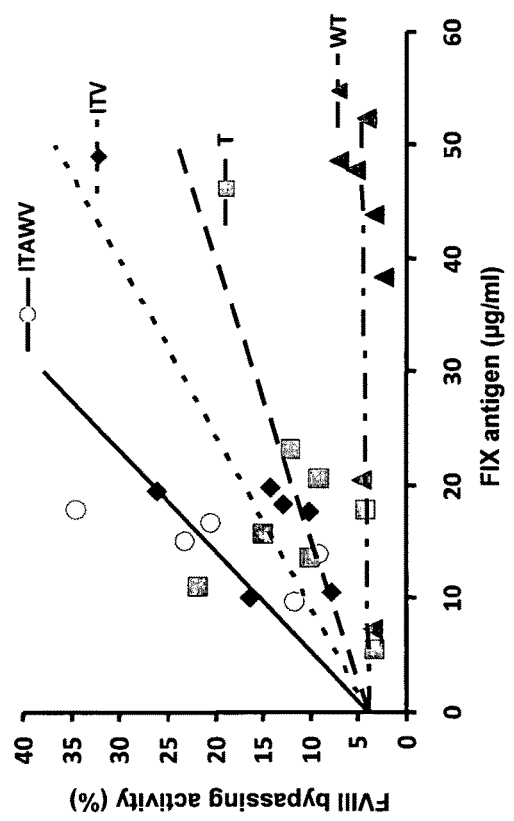

FIG. 5 FIX variants partially correct clotting times in F. VIII K.O. mice.

Non-viral minicircle vectors for liver-derived expression of F.IX at doses between 10 and 50 µg/mouse, either WT or variant [K265T (T), V181I/K265T/I383V (ITV) or V181I/K265T/R338A/S377W/I383V (ITAWV)], were injected into F.VIII K.O. mice by hydrodynamic injection technique. At day 3 post injection blood was drawn from the mice for F.IX antigen (ELISA) and F.VIII bypassing activity (one-stage assay in F.VIII deficient plasma) measurements in mouse plasma. While F.IX WT expressing mice showed a bypassing activity around baseline over all levels of expression, F.VIII bypassing activity of up to 35% of normal F.VIII activity was measured for the variants at high levels of expression (around 20 µg/ml). There was a good correlation between F.IX antigen levels and F.VIII bypassing activity for all variants with F.IX ITAWV showing the highest and F.IX T the lowest FVIII bypassing activity. Each data point represents a measurement of a single mouse.

Figure 6:
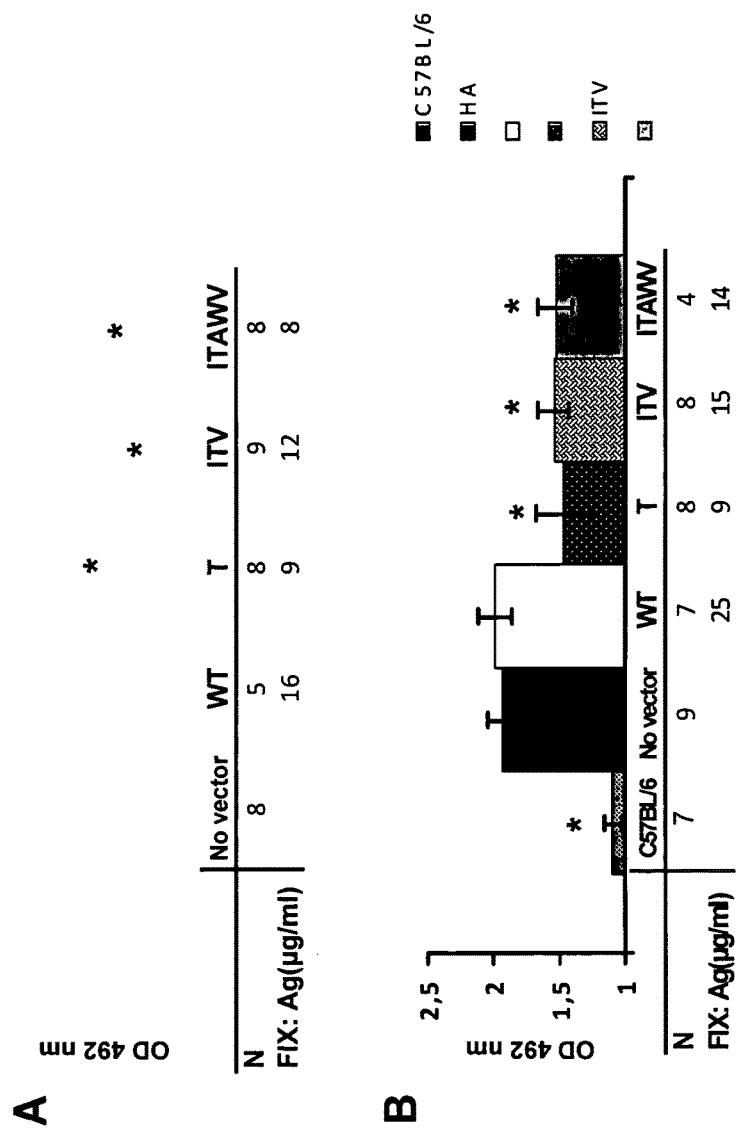

FIG. 6 F.IX variants stop bleeding in FVIII K.O. mice.

F.VIII K.O. mice expressing F.IX WT or variants [K265T (T), V181I/K265T/I383V (ITV) or V181I/K265T/R338A/S377W/I383V (ITAWV)] following non-viral gene transfer were challenged by tail clip assay. In short, mice were anesthetized and the tail pre-heated in 37° C. saline solution. The tails were then cut at either 1.5 mm (A) or 3 mm (B) diameter and blood was collected into the warm saline solution. After ten minutes the tails of the mice were sutured and cauterized to stop bleeding. Blood loss was quantified by optic density (OD 492 nm) measurement of the lost hemoglobin in the saline solution. There was a significant reduction in blood loss for all F.IX variant treated groups of mice compared to either F.IX WT expressing or not vector treated mice in both bleeding models. This improvement was a partial correction as seen in the more provocative 3 mm model in comparison to hemostatically normal C57BL/6 mice. Numbers of mice and average expression levels are shown for each group of mice below the graph. Each column represents mean values for blood loss with standard error of mean as error bars. *Student's t-test compared to F.IX WT <0.05.

Figure 7:
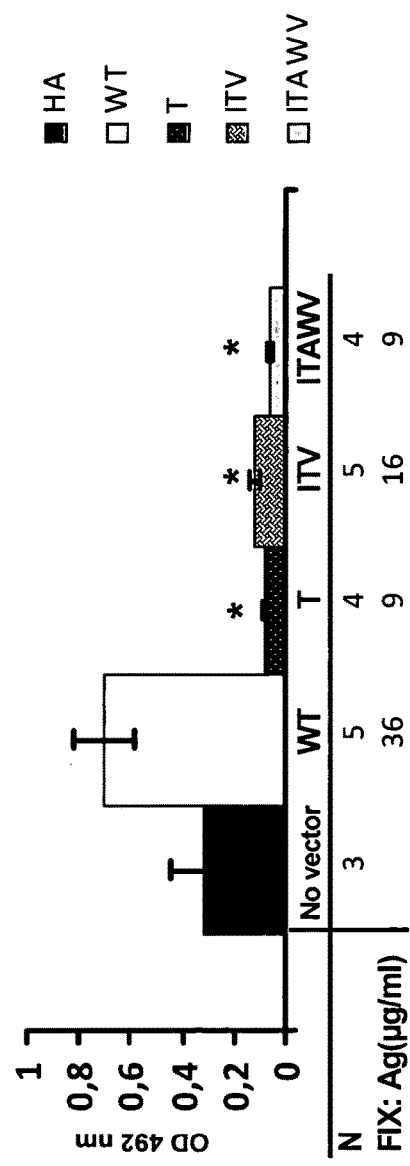

FIG. 7 FIX variants stop bleeding in F. VIII K.O. mice with high titers of inhibitory antibodies against F. VIII.

Inhibitory antibodies against F.VIII were induced in F.VIII K.O. mice by non-viral gene transfer to the liver using F.VIII gene transfer with a plasmid vector. Gene transfer was determined by F.VIII measurement at day 3 post injection. 6 weeks later we confirmed the presence of high titers (20.000 to 100.000 ng/ml) of anti-FVIII antibodies and the absence of residual F.VIII antigen and activity by one-stage and ELISA assay. Mice were then treated by minicircle gene transfer for F.IX WT or variant expression and challenged by tail clip assay on the third following day. Numbers of mice in each group and average F.IX expression levels are shown below the graph. Although there was some variation in blood loss among control groups (no vector and F.IX WT treated mice), the blood loss in all three variant groups [K265T (T), V181I/K265T/I383V (ITV) or V181I/K265T/R338A/S377W/I383V (ITAWV)] was significantly reduced. Each column represents mean values for blood loss with standard error of mean as error bars. *Student's t-test <0.05.

Figure 8:
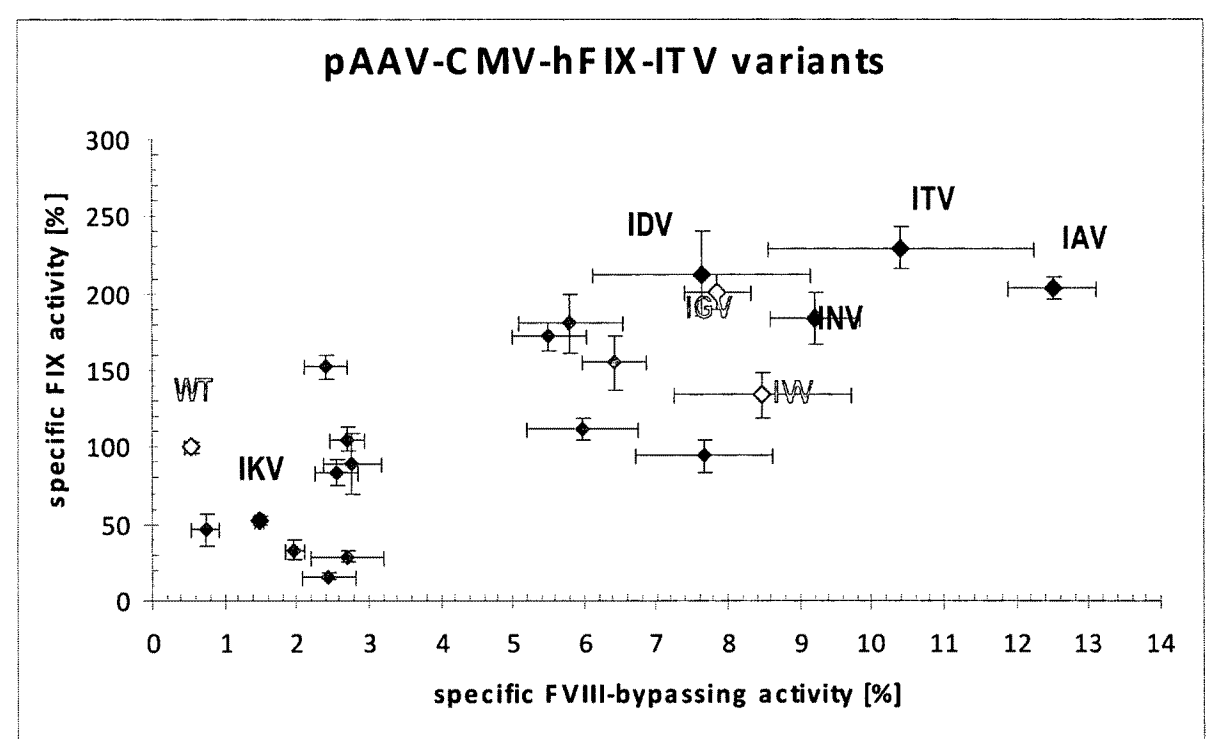

FIG. 8 Position 265 is the main determinant for F. VIII bypassing activity of FIX variants.

To investigate the role of position 265 in F.IX variants with F.VIII independent activity, all proteinogenic amino acids were introduced at this position in a FIX molecule which had the additional V181I and I383V substitutions. The variants were expressed in HEK 293 cells, F.IX antigen levels determined by ELISA, and F.IX activity in F.IX deficient and in deficient plasma was determined by one-stage assay, as described above. Each dot represents the mean value for a single variant with standard errors of mean as error bars. The experiments were performed in triplicates and repeated at least twice.

Wildtype (WT) refers to V181/K265/I383, ITV refers to V181I/K265T/I383V, IAV refers to V181I/K265A/I383V.

The Y-axis shows the F.IX specific activity (F.IX activity divided by F.IX antigen in percent), setting F.IX WT as 100%. The X-axis shows the same ratio, but this time the activity measurement was performed in F.VIII deficient plasma. Reversing residue 265 from Threonine to the natural occurring Lysine (V181I/265K/I383V, IKV) resulted in a near complete loss of F.VIII independent activity. Surprisingly, other amino acid substitutions, especially in the variants K265A/V181I/I383V, K265G/V181I/I383V, K265V/V181I/I383V, K265N/V181I/I383V, or K265D/V181I/I383V, resulted in similar F.VIII-bypassing activity than K265T/V181I/I383V, being highest for K265A/V181I/I383V. This result was unexpected, since the F.VIII independent activity for a factor IX variant carrying the single K265A substitution which was previously described was in a far lower range (Kolkman and Mertens, 2000).

EXAMPLES

Example 1

The inventors explored the hypothesis, that modification of the active site conformation of F.IX towards a state more likely observed when assembled in the tenase complex would result in a protein with increased activity in absence of F.VIII.

The mutations were chosen based on the structural studies comparing and substituting residues of F.IX by F.X available in the literature (Hopfner et al., 1997; Sichler et al., 2003).

The inventors first introduced the mutations Y259F/K265T/Y345T (FTT) into F.IX and expressed the protein in tissue culture. Basically no effect was seen on F.IX specific activity; however the activity in F.VIII-deficient plasma increased dramatically. Since this activity is still a small fraction of the F.IX specific activity (100% of F.IX antigen corresponds to 2% of "F.VIII-like" activity), the inventors concentrated the variant proteins to concentrations of 20,000 to 40,000 ng/ml (400-800% of normal plasma concentration). In this concentration "F.VIII-like" activities of up to over 30% could be measured, while no activity was detected for WT F.IX or negative controls.

Comparison of the activities of the FTT variant in F.VIII-, F.IX-, or F.X-deficient plasma compared to the wild-type protein (WT) is shown in FIG. 2.

Example 2

To further improve the properties of the FTT variant, the inventors combined the FTT variant with several other mutations in order to generate F.IX molecules with different properties.

Table 1 gives an overview of the tested mutations and the activity of the variants in F-VIII.- or F-IX-deficient plasma.

Example 3

Since (13) described an increased effect of the truncated F.IX (rf9) on chromogenic substrates only when all three substitutions (Y94F, K98T, and Y177T chymotryspin numbering) of the FTT variant were present at the same time, the inventors initially used the combined variant for the experiments.

However, the inventors also tested the single mutations and found surprisingly that the only substitution necessary is the K265T (i.e. K98T) variant and that the others are even worsening the protease activity in presence and absence of F.VIII (Table 1).

Example 4

The inventors further tested variants and combined them to obtain molecules with high F.IX activity in presence of F.VIII.

Table 3 shows several variants with more then 10-fold increase in activity. Also apparent from this table is the fact that combining mutations with desired increased activity leads to combined variants with highest activity levels. Some of the variants, like R338A/S377W, were also tested for their activity in absence of F.VIII (Table 1). However, only in combination with the K265T variant an enhanced effect on the F.VIII independent F.IX activity could be observed.

Example 5

To construct variants with desired properties the inventors combined single mutations with a desired effect to obtain variants with further increased desired high activities. For example, the K265T variant has 6.6% activity in absence of F.VIII and 191% activity in presence of F.VIII. To obtain the highest possible activity in absence of F.VIII but no or only moderate increase in presence of F.VIII, the inventors combined the K265T mutation with either mutation I383V or V181I. The resulting variants V181I/K265T and K265T/I383V had 9.0% and 8.7% activity in absence of F.VIII, and 219% and 139% activity in presence of F.VIII. This moderate increase in activity in absence of F.VIII could further be significantly improved by combining all three mutations to the variant V181I/K265T/I383V without increasing the activity in presence of F.VIII to 16.4% and 209%, respectively.

A summary of tested combinations is shown in Table 1 and the effects of single variants is summarized in Table 2.

Example 6

F.IX Variants Correct Clotting Time in Presence of Inhibitory Antibodies

To confirm functionality of F.IX variants in presence of inhibitory antibodies directed against FVIII we performed aPTT-based one stage F.VIII assays in plasma of patients with an acquired form of hemophilia A (FIG. 4). Normal control plasma, F.IX WT, or variants K265T (T) or V181I/K265T/I383V (ITV) were mixed into patient plasma at equal volumes (1:1). The mix was incubated at 37° C. for two hours and then clotting activity was determined in F.VIII deficient plasma. While normal control plasma did not or did only insufficiently normalize clotting times, the F.IX variants T and ITV led to a significant shortening of the clotting times at levels of 50% or 100% of normal human F.IX antigen levels, respectively. The observed coagulation function in presence of inhibitory anti-F.VIII antibodies is in good accordance with the previously listed values in F.VIII deficient plasma (Table 1). The results therefore confirm the function of the tested F.IX variants also in presence of high titers of F.VIII inhibitors.

Example 7

F.IX Variants Correct Coagulation In Vivo

In the following experiments we aimed to test, if F.IX variants could indeed improve hemostasis in vivo and therefore provide proof of concept for the feasibility of an approach using F.IX variants as bypassing therapeutics. For testing we used a non-viral minicircle vector system for liver-derived expression of F.IX. Vectors for WT or variant F.IX [K265T (T), V181I/K265T/I383V (ITV) or V181I/K265T/R338A/S377W/I383V (ITAWV)] were injected into the tail veins of F.VIII K.O. mice using hydrodynamic injection technique. At day 3 post injection blood was drawn from the mice for F.IX antigen (ELISA) and F.VIII bypassing activity (one-stage assay in F.VIII deficient plasma) measurements in mouse plasma. While F.IX WT expressing mice showed a bypassing activity around baseline over all levels of expression, F.VIII bypassing activity of up to 35% of normal F.VIII activity was measured for the variants at high levels of expression (around 20 µg/ml). There was a good correlation between F.IX antigen levels and F.VIII bypassing activity for all variants with F.IX ITAWV showing the highest and F.IX T the lowest F.VIII bypassing activity (FIG. 5). These results confirm the functionality of the variants also in the murine system. We then challenged different groups of mice by tail clip assay. The tails were then cut at either 1.5 mm (FIG. 6A) or 3 mm (FIG. 6B) diameter and blood was collected. After ten minutes bleeding was stopped and blood loss was quantified. There was a significant reduction in blood loss for all FAX variant treated groups of mice compared to either F.IX WT expressing or not vector treated mice in both bleeding models. This improvement was a partial correction as seen in the more provocative 3 mm model in comparison to non-hemophilic C57BL/6 mice. This is the first evidence that F.IX variants indeed could serve as hemostatically active therapeutics in vivo.

Example 8

F.IX Variants Stop Bleeding in Presence of Inhibitory Antibodies

Next, functionality of F.IX variants in presence of high titers of inhibitory antibodies against F.VIII was confirmed. Here fore, anti-F.VIII antibodies were induced in F.VIII K.O. mice using the inhibitor induction model introduced by C.Miao and co-workers (Ye et al., 2004). Initial F.VIII expression was obtained using non-viral F.VIII gene transfer to the liver using a plasmid vector. Six weeks later, we confirmed the presence of high titers (20.000 to 100.000 ng/ml) of anti-F.VIII antibodies and the absence of residual F.VIII antigen and activity by one-stage and ELISA assays. Mice were then treated by minicircle gene transfer for F.IX WT or variant expression and challenged by tail clip assay on the third following day (FIG. 7). The blood loss among control groups (no vector and FIX WT treated mice) was significantly higher compared to the bleeding in all three variant treated groups [K265T (T), V181I/K265T/I383V (ITV) or V181I/K265T/R338A/S377W/I383V (ITAWV)]. Therefore, the functionality of F.IX variants in both, in presence and in absence, of inhibitory antibodies to F.VIII was confirmed.

Example 9

In a further experiment, the inventors tested different amino acids in position 265, wherein the construct used furthermore contained mutations at positions 181 and 383 (namely V181I and I383V). The vector construct used was pAAV-CMV-hF.IX. The variants were expressed in HEK 293 cells, F.IX antigen levels determined by ELISA, and F.IX activity in F.IX deficient and ind F.VIII deficient plasma was determined by one-stage assay, as described above. Reversing residue 265 from Threonine to the natural occurring Lysine (V181I/265K/I383V, IKV) resulted in a near complete loss of F.VIII independent activity. Surprisingly, other amino acid substitutions, especially in the variants K265A/V181I/I383V, 1(265G/V181I/I383V, K265V/V181I/I383V, K265N/V181I/I383V, or K265D/V181I/I383V, resulted in similar F.VIII-bypassing activity than K265T/V181I/I383V, being highest for K265A/V181I/I383V. Results are shown in Table 4 and FIG. 8. As can be seen, mutants with small amino acid residues in position 265 show higher clotting activity, wherein the mutations K265T and K265A show the highest increase in clotting activity. This result was unexpected, since the F.VIII independent activity for a factor IX variant carrying the single K265A substitution which was previously described was in a far lower range (Kolkman and Mertens, Biochemistry 2000, 39, 7398-7405)

Material and Methods

Plasmid Constructs and Non Viral Vectors

Figure 3:
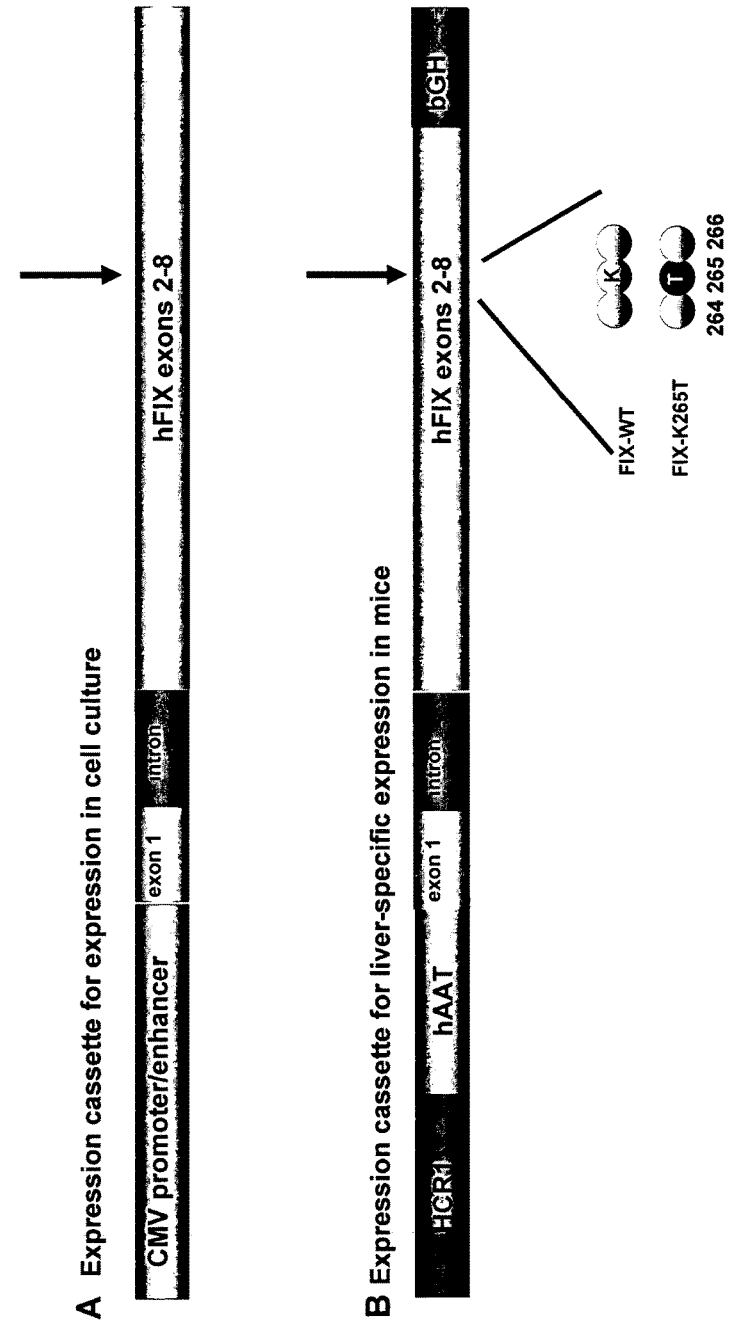

Two different expression vectors for FIX variants were employed for the experiments. The vectors for tissue culture (FIG. 3 A) consisted of F.IX with an 1.4 kb truncated intron 1 driven by a CMV promoter as previously described (Schuettrumpf et al., 2005). The nucleotide changes encoding for the desired variants were introduced into this plasmid by standard site directed mutagenesis.

The expression vector for liver directed gene transfer (FIG. 3B) consisted of the hepatic locus control region 1, the human alpha-1 anti-trypsin promoter, the F.IX mini-gene containing the truncated 1.4 kb intron 1, and a bovine growth hormone polyadenylation signal (HCR/hAAT-F.IX) as described (Miao et al., 2000) with minor modifications. The expression cassette was introduced into a mini-circle producer plasmid kindly provided by Mark Kay (Chen et al., 2005). This system allows the elimination of bacterial plasmid backbone sequence for circular DNA vectors. In short, a whole plasmid containing the expression cassette for F.IX flanked by integrase recognition sequences is grown in *E. coli* bacteria. An inducible phage ΦC31 integrase and the inducible endonuclease I-SceI together with its recognition site are located on the other (parental) part of the plasmid. After overnight growth, the integrase is activated by addition of arabinose. Activation of the integrase leads to the formation of two circles, one containing only the expression cassette, the other containing all the rest of the plasmid. Conditions (pH, temperature, and sodium content) are then adjusted for the endonuclease, which was similarly induced by the arabinose. This enzyme cuts in the bacterial plasmid backbone but not the expression cassette contained in the minicircle, so that the minicircle remains in the bacteria, while the rest of the plasmid is degraded. Minicircles were then purified over a regular one-step affinity column and residual bacterial DNA contaminants in the preparations were removed by linearization of the bacterial backbone with NruI restriction enzyme digest followed by exonucleolytical degradation with Plasmid-Safe ATP-Dependend DNase (Epicentre Biotechnologies, Madison, Wis.). Finally, we isolated the episomal DNA from the digests via phenol-chloroforme extraction resulting in recovery of highly pure minicircle (MC-HCR/hAAT-F.IX).

The F.VIII expression vector for inhibitor induction following liver-directed gene transfer in mice was constructed similar to the HCR/hAAT-F.IX construct with the difference, that F.IX was exchanged with the B-domain deleted F.VIII gene. Further, a plasmid vector containing the pSL1180 backbone instead of a minicircle vector was employed.

Expression of F.IX In Vitro for Variant Testing

HEK-293 were transfected with the CMV-F.IX plasmids by standard calcium phosphate transfection method and kept in serum free media with addition of 10 μg/ml vitamin K. 48 hours after transfection the supernatant of cells was collected and the cells were harvested. An aliquot of the supernatant was taken and tested for F.IX antigen levels and activity. For mutants with suspected F.VIII activity, the rest of the supernatant was concentrated using Vivaspin 20® (Viva Science AG, Hannover, Germany) concentration method. With this method concentrations of 25,000 ng/ml (500% of normal plasma activity) are easily obtained. This allowed accurate testing of the protease activity in F.VIII deficient plasma. Each time the experiment was performed, WT F.IX, F.IX S365R (no activity), and not transfected cells are used as controls. All experiments were repeated at least once and performed in triplicates.

F.VIII, F.IX, and F.VIII Inhibitor Assays

F.IX concentrations were determined using an enzyme-linked immunosorbent assay (ELISA) in which a monoclonal antibody to human F.IX, clone HIX-1 (Sigma, St Louis, Mo.), was used as capture antibody at dilution of 1:800; and as detecting antibody, peroxidase-conjugated polyclonal goat anti-human F.IX (Affinity Biologicals, Hamilton, ON) was used at dilution of 1:1000. F.IX functional activity was determined by a modified one-stage factor assay incubating 25 μl human FIX or FVIII-deficient plasma with 25 μl automated activated partial thromboplastin time (aPTT) reagent (Dade Behring, Marburg, Germany), and a total of 25 μl of a test sample that was undiluted (or when required, samples were diluted in imidazole buffer for 3 minutes at 37° C.). Then, 25 μl 25-mM CaCl2 was added, and time to clot formation was measured using a fibrometer. Antibodies to FVIII were measured by a specific ELISA to murine immunoglobulin G (IgG) subclasses (IgG1 and IgG2) as described (Schuettrumpf et al., 2005) with minor modifications by coating plates with 1 μg/ml purified recombinant FVIII (Cogenate, Bayer HealthCare, Leverkusen, Germany). The FVIII-activity in plasma of F.VIII inhibitor mice was determined by using Chromogenic FVIII:C Assay (Haemochrom Diagnostica, Essen, Germany). The determination of the FVIII antigene levels was performed using an ELISA kit from American Diagnostica (Pfungstadt, Germany).

Mouse Models

All animal procedures were approved by the local animal care, protection and use authorities. Mice deficient in FVIII were obtained from The Jackson Laboratory (Bar Harbour, Me., USA). C57Bl/6 mice were purchased from Harlan (Indianapolis, Ind.). For non viral gene transfer vector was administered by hydrodynamic injection technique as previously described (Schuettrumpf et al., 2008). In short, non viral vectors at doses of 10 to 50 μg per mouse in a volume of 2 ml physiological saline solution were injected into the tail vein of mice in 5 to 8 seconds. During the following experiments blood was then taken from the mice either by retro-orbital bleeding, or by bleeding following tail cut.

Blood Loss Assays

Tail-bleedings were performed blinded to the injected vector. Mice were anesthetized and distal tail (1.5 or 3 mm of diameter) was cut and immediately immersed in 37° C. saline solution. The blood loss was determined by measuring the absorbance of hemoglobin (A492 nm) in the saline solution in which the tail was placed, as reported. Schuettrumpf et al., 2005.

TABLE 1

Clotting activities of factor IX variants in absence and presence of F.VIII.

| Variants | Activity (%) without F.VIII | S.E.M. | Activity (%) with F.VIII | S.E.M. |
|---|---|---|---|---|
| R338A + S377W | 0.0 | 0.1 | 1086.6 | 125.5 |
| wild type | 0.0 | 0.1 | 100.0 | 3.7 |
| Y259F | 0.0 | 0.1 | 96.9 | 11.1 |
| Y345T | 0.0 | 0.0 | 50.9 | 8.1 |
| S365R | 0.0 | 0.0 | 0.0 | 0.3 |
| E245K + K265T | 0.2 | 0.1 | 21.6 | 7.1 |
| G4Y + Y259F + K265T + Y345T | 1.2 | 0.3 | 110.5 | 12.0 |
| N34D + Y259F + K265T + Y345T | 1.8 | 0.1 | 36.7 | 0.8 |
| Y259F + K265T + Y345T + R358A | 2.0 | 0.2 | 54.6 | 6.2 |
| Y259F + K265T + Y345T | 2.0 | 0.1 | 73.2 | 6.3 |
| Y259F + K265T + Y345T + E388G | 2.1 | 0.8 | 24.4 | 2.1 |
| Y259F + K265T + Y345T + F353Y | 2.1 | 0.4 | 57.1 | 6.8 |
| F25Y + Y259F + K265T + Y345T | 2.3 | 0.1 | 45.6 | 1.3 |
| Y259F + K265T + Y345T + S377W | 2.6 | 0.2 | 94.9 | 10.4 |
| Y259F + K265T + I290L + Y345T | 2.8 | 0.7 | 60.1 | 8.4 |
| Y259F + K265T + Y345T + S360A | 2.8 | 0.2 | 64.4 | 3.6 |
| Y259F + K265T + Y345T + I383V + E388G | 3.1 | 1.3 | 39.7 | 3.5 |
| V217L + Y259F + K265T + Y345T | 3.2 | 0.5 | 62.3 | 8.3 |
| Y259F + K265T + Y345T + I383V | 3.5 | 0.3 | 67.1 | 5.3 |
| Y259F + K265T + R338A + T340S + Y345T | 3.9 | 0.3 | 214.6 | 21.9 |
| V181I + Y259F + K265T + Y345T | 4.0 | 0.6 | 50.9 | 2.0 |
| D85A + K265T | 5.2 | 1.3 | 188.1 | 37.5 |
| K265T + S360A + I383V | 5.3 | 1.3 | 104.2 | 23.1 |
| V253I + K265T | 5.5 | 0.8 | 187.2 | 29.3 |

TABLE 1-continued

Clotting activities of factor IX variants
in absence and presence of F.VIII.

| Variants | Activity (%) without F.VIII | S.E.M. | Activity (%) with F.VIII | S.E.M. |
|---|---|---|---|---|
| Y259F + K265T | 5.9 | 0.9 | 141.0 | 20.5 |
| K265T + S360A | 5.9 | 0.5 | 187.0 | 19.8 |
| V217L + K265T | 6.0 | 0.9 | 259.9 | 39.2 |
| K265T | 6.6 | 0.7 | 191.1 | 14.0 |
| R338A + K265T | 7.1 | 0.6 | 658.2 | 86.4 |
| K265T + R338A + I383V | 8.1 | 1.4 | 480.2 | 80.9 |
| K265T + I383V | 8.7 | 1.1 | 138.7 | 15.8 |
| V181I + K265T | 9.0 | 0.8 | 219.2 | 22.4 |
| V181I + K265T + I383V | 16.4 | 2.1 | 204.9 | 28.9 |
| V181I + K265T + R338A + S377W + I383V | 21.9 | 3.9 | 1637.9 | 335.9 |

Values are shown in percent, being 100% the activity of wild type factor IX in normal human pool plasma with normal human levels of both F.IX and F.VIII. Standard error of mean (S.E.M.)

TABLE 2

Factor IX variants for the treatment of hemophilia B. Proteins show altered factor IX specific activity (in percent compared to wild type F.IX).

| Variants | F.IX Activity (%) | S.E.M. |
|---|---|---|
| G4Y + V10K | 41 | 3 |
| G4Y + R37T | 54 | 4 |
| S340T + R338A + Y345T | 87 | 13 |
| WT | 100 | 5 |
| G4Y | 101 | 8 |
| G4Y + Y1A | 102 | 12 |
| S377W | 218 | 27 |
| R338A | 552 | 68 |
| R338A + S377W | 841 | 138 |
| S360A + R338A + S377W | 938 | 94 |
| V86A + R338A + S377W | 1076 | 77 |
| G4Y + R338A + S377W | 1284 | 335 |

F.IX activity in absence of F.VIII is below detection limits by one-stage assay method. Standard error of mean (S.E.M.)

TABLE 3

Effect of mutations additional to K265T on F.IX clotting activity in absence or presence of F.VIII.

| Mutation | Activity without F.VIII | Activity with F.VIII |
|---|---|---|
| R338A | U | U |
| V181I | U | N (U) |
| I383V | U | D |
| V86A | N (U) | U |
| S377W | N (U) | U |
| V217L | N (U) | N (U) |
| I290L | N (U) | N (D) |
| F25Y | N (U) | D |
| F353Y | N (U) | D |
| D85A | N (D) | N (D) |
| V253I | N (D) | N (D) |
| Y259F | N (D) | N (D) |
| E388G | N (D) | D |
| N34D | N (D) | D |
| R358A | N (D) | D |
| S360A | N | N (D) |
| T340S | N | N |
| Y345T | D | D |
| G4Y | D | U |
| E245K | D | D |

U: clotting activity up; D: clotting activity down; N: no change in clotting activity, wherein N(U): tendency up or N(D): tendency down.

TABLE 4

Clotting activities of factor IX variants in absence and presence of F.VIII. Values are shown in percent, being 100% the activity of wild type factor IX in normal human pool plasma with normal human levels of both F.IX and F.VIII.

aPTT

| Mutation | F.IX activity [%] ± SEM | F.VH-bypassing activity [%] ± SEM |
|---|---|---|
| WT | 100 ± 3 | 0.52 ± 0.7 |
| ITV | 230 ± 14 | 10.4 ± 1.85 |
| IAV | 204 ± 7 | 12.51 ± 0.61 |
| IKV | 52 ± 3 | 1.49 ± 0.07 |
| ICV | 33 ± 6 | 1.97 ± 0.14 |
| IDV | 213 ± 27 | 7.63 ± 1.52 |
| IEV | 181 ± 19 | 5.8 ± 0.72 |
| IFV | 155 ± 18 | 6.42 ± 0.44 |
| IGV | 201 ± 12 | 7.96 ± 0.47 |
| IHV | 152 ± 8 | 7.66 ± 0.95 |
| IIV | 172 ± 10 | 5.51 ± 0.53 |
| ILV | 94 ± 11 | 2.41 ± 0.29 |
| IMV | 89 ± 20 | 2.78 ± 0.4 |
| INV | 184 ± 17 | 9.21 ± 0.62 |
| IPV | 29 ± 3 | 2.7 ± 0.5 |
| IQV | 105 ± 8 | 2.71 ± 0.25 |
| IRV | 46 ± 11 | 0.73 ± 0.2 |
| ISV | 112 ± 7 | 5.97 ± 0.77 |
| IVV | 134 ± 15 | 8.49 ± 1.23 |
| IWV | 16 ± 2 | 2.44 ± 0.37 |
| IYV | 83 ± 9 | 2.56 ± 0.29 |

Standard error of mean (S.E.M.)
Wildtype (WT) refers to V181/K265/I383, ITV refers to V181I/K265T/I383V, IAV refers to V181I/K265A/I383V and so one.
F.IX activity refers to activity with F.VIII;
F.VIII bypassing activity refers to activity without F.VIII The features disclosed in the foregoing description, in the claims and/or in the accompanying drawings may, both separately and in any combination thereof, be material for realizing the invention in diverse forms thereof.

REFERENCES

Arruda et al. *Blood* 2004, 104:85.
Chang et al. THE JOURNAL OF BIOLOGICAL CHEMISTRY Vol. 277, No. 28, Issue of July 12, pp. 25393-25399, 2002.
Chang et al. THE JOURNAL OF BIOLOGICAL CHEMISTRY Vol. 273, No. 20, Issue of May 15, pp. 12089-12094, 1998.
Chen Z Y, He C Y, Kay M A. Improved production and purification of minicircle DNA vector free of plasmid bacterial sequences and capable of persistent transgene expression in vivo. *Hum Gene Ther.* 2005; 16(1):126-31.
Davie, E. W., Fujikawa, K., and Kisiel, W. (1991) *Biochemistry* 30, 10363-10370.
DiScipio, R. G., Hermodson, M. A., Yates, S. G., and Davie, E. W. (1977) *Biochemistry* 16, 698-706.
Di Scipio R G, Kurachi K and Davie E W (1978) Activation of human factor IX (Christmas factor). *J Clin Invest,* 61, 1528-1538.
Duffy E J and Lollar P (1992) Intrinsic pathway activation of factor X and its activation peptide-deficient derivative, factor Xdes-143-191. *J Biol Chem,* 267, 7821-7827.
Fujikawa, K., Legaz, M. E., Kato, H., and Davie, E. W. (1974) *Biochemistry* 13, 4508-4516.
Furie B and Furie B C (1988) The molecular basis of blood coagulation. *Cell,* 53, 505-518.
Giannelli, F., Green, P. M., Sommer, S. S., Poon, M., Ludwig, M., Schwaab, R., Reitsma, P. H., Goossens, M., Yoshioka, A., Figueiredo, M. S., and Brownlee, G. G. (1998) *Nucleic Acids Res.* 26, 265-268.

Hartmann R, Dockal M, Kammlander W, Panholzer E, Scheiflinger F (2007) Blood (ASH Annual Meeting Abstracts) vol. 110 no. 11: page 791A, Abstract 2694.

Hockin M F, Jones K C, Everse S J, Mann K G. (2002) *J Biol Chem.* 277, 18322-33.

Hopfner K P, Brandstetter H, Karcher A, Kopetzki E, Huber R, Engh R A, Bode W. (1997) EMBO J. 16(22):6626-35.

Kolkman and Mertens, Biochemistry 2000, 39, 7398-7405 (K265A Mutante)

Kurachi and Davie (1982) PNAS 79:6461-6464.

Langdell R D, Wagner R H, Brinkhous K M (1953). "Effect of antihemophilic factor on one-stage clotting tests; a presumptive test for hemophilia and a simple one-stage antihemophilic factor assy procedure". *J. Lab. Clin. Med.* 41 (4): 637-47.

Lindquist, P. A., Fujikawa, K., and Davie, E. W. (1978) *J Biol. Chem.* 253, 1902-1909.

Mann et al. *Arterioscler Thromb Vasc Biol.* 2003; 23:17-25.

McRae B J, Kurachi K, Heimark R L, Fujikawa K, Davie E W and Powers J C (1981) Mapping the active sites of bovine thrombin, factor IXa, factor Xa, factor XIa, factor XIIa, plasma kallikrein, and trypsin with amino acid and peptide thioesters: development of new sensitive substrates. *Biochemistry,* 20, 7196-7206.

Miao C H, Ohashi K, Patijn G A, Meuse L, Ye X, Thompson A R, Kay M A. Inclusion of the hepatic locus control region, an intron, and untranslated region increases and stabilizes hepatic factor IX gene expression in vivo but not in vitro. *Mol Ther.* 2000; 1(6):522-32.

Schuettrumpf J, Herzog R W, Schlachterman A, Kaufhold A, Stafford D W, Arruda V R. (2005) *Blood.* 105(6):2316-23.

Schuettrumpf J, Milanov P, Roth S, Seifried E, Tonn T. Non-viral gene transfer results in therapeutic factor IX levels in haemophilia B mice, *Haemost.* 2008; 1:S92-95.

Sichler K, Kopetzki E, Huber R, Bode W, Hopfner K P, Brandstetter H. Physiological fIXa activation involves a cooperative conformational rearrangement of the 99-loop. (2003) *J Biol Chem.* 278(6):4121-6.

Ye et al. MOLECULAR THERAPY Vol. 10, No. 1, July 2004, p 117.

The invention claimed is:

1. A variant of factor IX (F.IX) or activated factor IX (F.IXa) which is characterized in that it has clotting activity in the absence of its cofactor, wherein the cofactor is factor VIII (F.VIII) or activated factor VIII (F.VIIIa), said variant of factor IX or activated factor IX comprising an amino acid substitution in position 265 in combination with amino acid substitution V181I, wherein the amino acid substitution in position 265 is selected from K265T, K265A, K265D, K265E, K265F, K265G, K265H, K265I, K265N, K265S and K265V, wherein the variant factor IX or activated factor IX does not encompass variant Y259F/K265T/Y345F/I383V/E388G or variant Y259F/A261K/K265T/Y345F/I383V/E388G, and wherein said amino acid substitutions are made at positions in reference to amino acids 47 to 461 of the amino acid sequence of SEQ ID NO. 2, and wherein the blood clotting activity of said variant is at least 1% as measured in an aPTT assay in the absence of F.VIII compared to wildtype having 0% clotting activity in the absence of F.VIII and 100% activity in the presence of F.VIII.

2. The variant F.IX or F.IXa of claim 1, wherein the amino acid substitution in position 265 is selected from K265T, K265A, K265G, K265V, K265N and K265D.

3. The variant FAX or F.IXa of claim 1, further comprising an amino acid substitution in position 338 and/or 377.

4. The variant F.IX or F.IXa of claim 1, selected from
variant K265T/V181I,
variant K265T/I383V,
variant K265T/V181I/I383V,
variant K265T/V181I/I383V/R338A/S377W,
variant K265A/V181I/I383V, and
variant K265A/V181I/I383V/R338A/S377W.

5. The variant F.IX or F.IXa of claim 1, selected from a variant having an amino acid substitution in position 265 selected from K265T, K265A, K265D, K265E, K265F, K265G, K265H, K265I, K265N, K265S and K265V, in combination with amino acid substitution V181I and amino acid substitution I383V.

6. The variant, according to claim 5, wherein the variant is selected from
variant K265T/V181I/I383V,
variant K265A/V181I/I383V,
variant K265G/V181I/I383V,
variant K265V/V181I/I383V,
variant K265N/V181I/I383V,
variant K265D/V181I/I383V,
variant K265E/V181I/I383V,
variant K265F/V181I/I383V,
variant K265H/V181I/I383V,
variant K265I/V181I/I383V, and
variant K265S/V181I/I383V.

7. The variant of F.IX or F.IXa of claim 1, comprising a further compound or moiety attached to the variant of F.IX or F.IXa.

8. The variant of F.IX or F.IXa, according to claim 7, wherein the further compound or moiety is selected from proteins, labels and polymers.

9. The variant of F.IX or F.IXa, according to claim 7, wherein the further compound or moiety is covalently attached to the variant of F.IX or F.IXa.

10. A pharmaceutical composition comprising a variant F.IX or F.IXa of claim 1, or a nucleic acid encoding said variant, and optionally one or more pharmaceutically acceptable carriers and/or excipients.

11. A method for the prevention and/or treatment of a bleeding disorder or bleeding, wherein said method comprises administering to a subject in need of such prevention and/or treatment a variant F.IX or F.IXa of claim 1, a nucleic acid encoding said variant, or a pharmaceutical composition comprising said variant and/or said nucleic acid.

12. The method according to claim 11, wherein the bleeding disorder is hemophilia A, hemophilia caused or complicated by inhibitory antibodies to factor F.VIII or F.VIIIa; or hemophilia B.

13. The method, according to claim 11, wherein the bleeding disorder or bleeding is a bleeding disorder where by-passing agents are used; a severe hepatic disease; a high-risk surgical procedure; traumatic blood loss; bone marrow transplantation; a thrombocytopenia or platelet function disorder; an urgent reversal of oral anticoagulation; a congenital deficiency of factors V, VII, X, and XI; von Willebrand disease with inhibitors to von Willebrand factor; blood loss in connection with a large injury; cerebral bleeding; or thrombocyte function disorder.

14. The method, according to claim 11, used for cellular therapy, gene therapy, or protein infusion therapy.

15. The variant F.IX or activated F.IXa of claim 1, further comprising an amino acid substitution at position 383.

16. The variant F.IX or activated F.IXa of claim 15, wherein the amino acid substitution at position 383 is I383V.

17. The variant F.IX or activated F.IXa of claim 1, wherein the clotting activity of said variant is at least 8% as measured in an aPTT assay in the absence of F.VIII compared to wildtype having 0% clotting activity in the absence of F.VIII and 100% activity in the presence of F.VIII.

18. The variant F.IX or activated F.IXa of claim 16, wherein the clotting activity of said variant is at least 10% as measured in an aPTT assay in the absence of F.VIII compared to wildtype having 0% clotting activity in the absence of F.VIII and 100% activity in the presence of F.VIII.

* * * * *

SEQUENCE LISTING

<160> NUMBER OF SEQ ID NOS: 2

<210> SEQ ID NO 1
<211> LENGTH: 1386
<212> TYPE: DNA
<213> ORGANISM: Homo sapiens

<400> SEQUENCE: 1

```
atgcagcgcg tgaacatgat catggcagaa tcaccaggcc tcatcaccat ctgccttta      60 ggatatctac tcagtgctga atgtacagtt tttcttgatc atgaaaacgc caacaaaatt    120
ctgaatcggc aaagaggta taattcaggt aaattggaag agtttgttca agggaacctt    180
gagagagaat gtatggaaga aaagtgtagt tttgaagaag cacgagaagt ttttgaaaac    240
actgaaagaa caactgaatt ttggaagcag tatgttgatg gagatcagtg tgagtccaat    300
ccatgtttaa atggcggcag ttgcaaggat gacattaatt cctatgaatg ttggtgtccc    360
tttggatttg aaggaaagaa ctgtgaatta gatgtaacat gtaacattaa gaatggcaga    420
tgcgagcagt tttgtaaaaa tagtgctgat aacaaggtgg tttgctcctg tactgaggga    480
tatcgacttg cagaaaacca gaagtcctgt gaaccagcag tgccatttcc atgtggaaga    540
gtttctgttt cacaaacttc taagctcacc cgtgctgaga ctgtttttcc tgatgtggac    600
tatgtaaatt ctactgaagc tgaaaccatt ttggataaca tcactcaaag cacccaatca    660
tttaatgact tcacgcgtgt tgttggtgga gaagatgcca aaccaggtca attcccttgg    720
caggttgttt tgaatggtaa agttgatgca ttctgtggag gctctatcgt taatgaaaaa    780
tggattgtaa ctgctgccca ctgtgttgaa actggtgtta aaattacagt tgtcgccggc    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga atcagctttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac cccatgttac tgaagtgaa   1260 gggaccagtt tcttaactgg aattattagc tggggtgaag agtgtgcaat gaaaggcaaa   1320
```

-continued

```
tatggaatat ataccaaggt atcccggtat gtcaactgga ttaaggaaaa aacaaagctc    1380
acttaa                                                              1386
```

<210> SEQ ID NO 2
<211> LENGTH: 461
<212> TYPE: PRT
<213> ORGANISM: Homo sapiens

<400> SEQUENCE: 2

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350
```

-continued

```
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr
    450                 455                 460
```